(12) United States Patent
Van Voast et al.

(10) Patent No.: US 9,347,868 B2
(45) Date of Patent: May 24, 2016

(54) METHODS AND SYSTEMS FOR RAPIDLY TESTING ADHESION

(71) Applicant: The Boeing Company, Seal Beach, CA (US)

(72) Inventors: Peter J. Van Voast, Normandy Park, WA (US); Kay Youngdahl Blohowiak, Issaquah, WA (US); John Christopher Osborne, Seattle, WA (US); Marcus Anthony Belcher, Sammamish, WA (US)

(73) Assignee: The Boeing Company, Chicago, IL (US)

( * ) Notice: Subject to any disclaimer, the term of this patent is extended or adjusted under 35 U.S.C. 154(b) by 271 days.

(21) Appl. No.: 14/103,726

(22) Filed: Dec. 11, 2013

(65) Prior Publication Data
US 2014/0326074 A1 Nov. 6, 2014

Related U.S. Application Data

(60) Provisional application No. 61/818,598, filed on May 2, 2013.

(51) Int. Cl.
*G01N 19/04* (2006.01)

(52) U.S. Cl.
CPC ........ *G01N 19/04* (2013.01); *G01N 2203/0091* (2013.01); *G01N 2203/0298* (2013.01); *Y10T 156/10* (2015.01)

(58) Field of Classification Search
CPC ............ G01N 9/04; G01N 2203/0025; G01N 2203/0282; G01N 2203/0091; G01N 3/08; G01N 3/24

USPC ............................................ 73/150 A, 150 R
See application file for complete search history.

(56) References Cited

U.S. PATENT DOCUMENTS

| | | |
|---|---|---|
| 3,962,498 A | 6/1976 | Owston |
| 6,551,407 B2 | 4/2003 | Drzal et al. |
| 6,565,927 B1 | 5/2003 | Bhurke et al. |
| 6,622,568 B2 | 9/2003 | Nelson et al. |
| 6,692,595 B2 | 2/2004 | Wheatley et al. |
| 6,848,321 B2 | 2/2005 | Bossi et al. |

(Continued)

FOREIGN PATENT DOCUMENTS

DE WO 2011157739 A1 * 12/2011 ............... G01N 3/42

OTHER PUBLICATIONS

Turaga et al. "Improved Design for Metallic and Composite Single-Lap Joints" Journal of Aircraft, vol. 45, No. 2, Mar.-Apr. 2008. <http://arc.aiaa.org/doi/pdf/10.2514/1.28934>.*

(Continued)

*Primary Examiner* — Lisa Caputo
*Assistant Examiner* — Jonathan Dunlap
(74) *Attorney, Agent, or Firm* — DASCENZO Intellectual Property Law, P.C.

(57) ABSTRACT

Adhesion testing systems, methods of fabrication, and methods of testing are disclosed. Test systems include test coupons with non-metallic test adherends. Test coupons are configured to test bonds to the non-metallic test adherends under peeling stress and/or shearing stress. Test methods are simplified and rapid as compared to standard adhesion tests and include methods of accelerated environmental testing. Test methods also are adapted for qualitative and quantitative measurement of bond performance.

16 Claims, 12 Drawing Sheets

(56) References Cited

U.S. PATENT DOCUMENTS

| | | | |
|---|---|---|---|
| RE39,839 E | 9/2007 | Wheatley et al. | |
| 7,507,312 B2 | 3/2009 | Bossi et al. | |
| 7,509,876 B1 | 3/2009 | Sokol et al. | |
| 8,043,449 B1* | 10/2011 | Przybelinski | G01N 3/02 156/350 |
| 8,342,017 B1* | 1/2013 | Bossi | G01N 19/04 73/150 A |
| 8,386,194 B1* | 2/2013 | Baldwin | G01N 13/02 702/30 |
| 8,616,050 B1* | 12/2013 | Dan-Jumbo | G01N 19/04 73/150 A |
| 9,021,874 B2* | 5/2015 | Bethke | G01N 3/42 73/150 A |
| 2007/0149080 A1 | 6/2007 | Asahara et al. | |
| 2010/0181017 A1 | 7/2010 | Shinoda et al. | |
| 2010/0285265 A1 | 11/2010 | Shinoda et al. | |
| 2013/0112005 A1* | 5/2013 | Bethke | G01N 3/42 73/799 |

OTHER PUBLICATIONS

Brian D. Flinn, "Improving Adhesive Bonding of Composites Through Surface Characterization," The Joint Advanced Materials and Structures Center of Excellence [PowerPoint Presentation].

Brian D. Flinn and Molly Phariss, "Improving Adhesive Bonding of Composites Through Surface Characterization," The Joint Advanced Materials and Structures Center of Excellence [PowerPoint Presentation].

R.G. Dillingham, S. Conyne-Rapin, F. J. Boerio, R. H. Bossi and R. Crane, "Surface Preparation of Composite Materials for Adhesive Bonding," Proc. 26th Annual Meeting of the Adhesion Society, Myrtle Beach, SC, Feb. 2003.

Richard Bossi, Kevin Housen and William Shepherd, "Application of Stress Waves to Bond Inspection," SAMPE 2004, Long Beach, CA., May 16-20, 2004.

Richard Bossi, Kevin Housen and Craig Walters, "Bond Strength Measurement Using a Laser Bond Inspection Device," SAMPE 2004, May 16-20, Long Beach, CA.

Richard Bossi, Robert Carlsen, F. James Boerio and Giles Dillingham, "Composite Surface Preparation QA for Bonding," 50th International SAMPE Symposium, Long Beach, CA, May 1-5, 2005.

Molly K.M. Phariss, Brian D. Flinn, Bjorn Ballien, William Grace, and Peter J. Van Voast, "Evaluation of Peel-Ply Materials on Composite Bond Quality," Presentation at SAMPE Fall 2005, Seattle, WA, Oct. 31-Nov. 3, 2005.

Brian D. Flinn and Molly Phariss, "The Effect of Peel-Ply Surface Preparation Variables on Bond Quality," DOT/FAA/ AR-06/28, Final Report, Aug. 2006.

Brian D. Flinn, Brian K. Clark, Jeffrey Satterwhite, and Peter J. Van Voast, "Influence of Peel Ply Type on Adhesive Bonding of Composites," SAMPE 2007, Seattle, WA, 2007.

ASTM International, ASTM D 3165, "Standard Test Method for Strength Properties of Adhesives in Shear Tension Loading of Single-Lap-Joint Laminated Assemblies," 2007.

ASTM International, ASTM D 5528, "Standard Test Method for Mode I Interlaminar Fracture Toughness of Unidirectional Fiber-Reinforced Polymer Matrix Composites," 2007.

Richard Bossi, Kevin Housen, Craig Walters and David Sokol, "Laser Bond Testing," Materials Evaluation, vol. 67, No. 7, Jul. 2009, pp. 819-827.

Kay Y. Blohowiak, Peter J. Van Voast, Paul H. Shelley and Jacob W. Grob, "Nonchemical Surface Treatments Using Energetic Systems for Structural Adhesive Bonding," SAMPE 2010, Seattle, WA, May 17-20, 2010.

Peter J. Van Voast, Paul H. Shelley, Richard L. Blakley, C. Brent Smith, Melanie P. Jones, Ashley C. Tracey, Brian D. Flinn, Giles Dillingham and Brietta Oakley, "Effect of Varying Levels of Peel Ply Contamination on Adhesion Threshold," SAMPE 2010, Seattle, WA, May 17-20, 2010.

Peter J. Van Voast, Paul H. Shelley, Richard L. Blakley, C. Brent Smith, Melanie P. Jones, Ashley C. Tracey, Brian D. Flinn, Giles Dillingham and Brietta Oakley, "Effect of Varying Levels of Peel Ply Contamination on Adhesion Threshold," Presentation at SAMPE 2010, Seattle, WA, May 17-20, 2010.

ASTM International, ASTM D 5573, "Standard Practice for Classifying Failure Modes in Fiber-Reinforced-Plastic (FRP) Joints," 2012.

ASTM International, ASTM D 1781, "Standard Test Method for Climbing Drum Peel for Adhesives," 2012.

Peter J. Van Voast, Kay Y. Blohowiak, John C. Osborne, and Marcus A. (Tony) Belcher, "Rapid Test Methods for Adhesives and Adhesion," SAMPE 2013, Long Beach, CA, May 2013.

Peter J. Van Voast, Kay Y. Blohowiak, John C. Osborne, and Marcus A. (Tony) Belcher, "Rapid Test Methods for Adhesives and Adhesion," Presentation at SAMPE 2013, Long Beach, CA, May 2013.

* cited by examiner

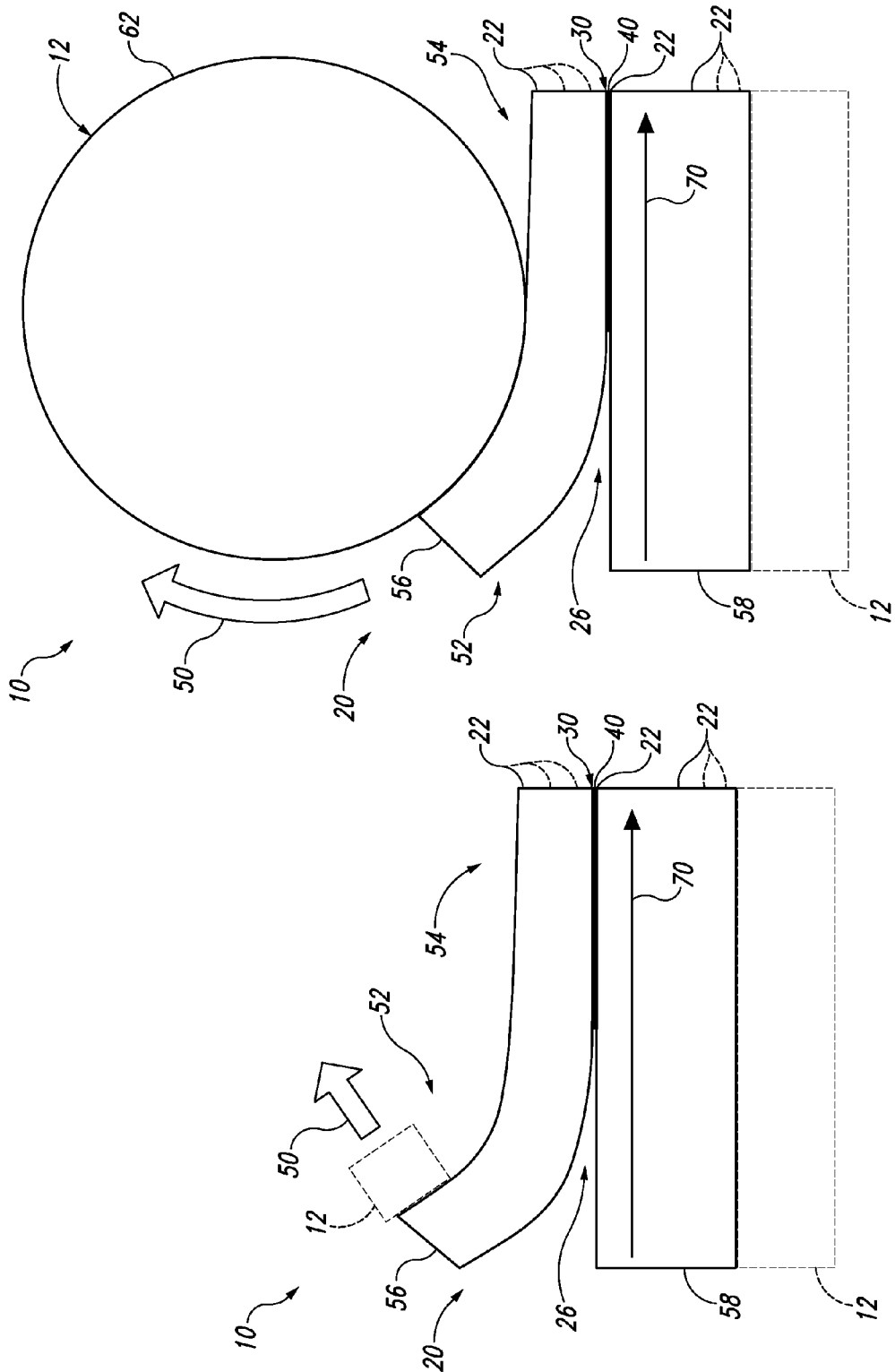

METHODS AND SYSTEMS FOR RAPIDLY TESTING ADHESION

RELATED APPLICATION

This application claims priority under 35 U.S.C. §119(e) to U.S. Provisional Application No. 61/818,598, filed May 22, 2013. The complete disclosure of which is incorporated herein by reference for all purposes.

FIELD

The present disclosure relates to methods and systems for rapidly testing adhesion.

BACKGROUND

Joints between components are of great importance in structural design in such industries as aerospace, transportation, and medicine. Mechanically fastened joints leave material discontinuities between components and produce localized, highly stressed areas. Adhesive joints may effectively replace mechanically fastened joints in certain situations. Adhesive joints may form a continuous bond between components, minimizing material discontinuities, and may distribute stress across the bonded joint, minimizing stress concentration. Further, adhesive joints may be tailored to the material properties of the bonded components, e.g., the properties of fiber-reinforced plastics (sometimes referred to as fiber-reinforced polymers or fiber-reinforced composites).

However, adhesion and adhesive joints are less well understood than mechanical fastening mechanisms. Adhesive bond quality is dependent on many factors including chemical bonding, mechanical factors (e.g., interlocking parts), material compatibility, surface preparation, and surface chemistry. Moreover, ensuring and verifying a quality adhesive bond are difficult tasks. Microscopic differences in composition and chemical state may be the difference between a strong bond and a weak bond. Non-destructive testing (e.g., x-ray inspection, ultrasonic inspection) generally indicates only gross material discontinuities but typically fails to indicate adhesion parameters such as chemical state and contamination. Hence, careful characterization of adhesive bonding schemes is important to preparing a quality bond.

Bond quality may be tested by applying forces to a bonded joint until the joint fails. Such destructive testing is impractical for products in service but is suitable for test samples and test coupons embodying a sample adhesive bonding scheme. Adhesion testing protocols designed primarily for metallic components exist (e.g., ASTM D1781 and ASTM D3165 published by ASTM International), but they require precise set-up, calibration, and measurement, and, in some cases, simply are not suitable for adhesion between non-metallic components. Further, adhesion testing protocols typically quantitate the strain energy release rate of a bond as it fails, requiring careful execution of the protocol and measurement of the results. Hence, there is a need for rapid, simplified adhesion testing protocols suitable for non-metallic components, which include simplified determination of results.

SUMMARY

The present disclosure includes methods of fabricating layered test coupons configured for peeling testing and/or shearing testing of adhesive bonds to non-metallic adherends. Fabrication methods may include incorporating a plurality of test bonds within a test structure. Fabrication methods may include environmental conditioning of test structures including test bonds prior to assembling the final test coupon.

A layered test coupon may be fabricated by adhering a first test adherend with a first test adhesive to a first location on a base support to create a first test bond, adhering a second test adherend with a second test adhesive to a second location, adjacent the first location, on the base support to create a second test bond, bonding the first test adherend to a peeling support, and bonding the second test adherend to the peeling support.

A layered test coupon may be fabricated by adhering a rigid test adherend with a test adhesive to a peeling support to create a test bond. A layered test coupon may be fabricated by adhering a test adherend with a test adhesive to a peeling support to create a test bond, and bonding the test adherend to a rigid base support.

A layered test coupon may be fabricated by adhering a test adherend with a test adhesive to a first peeling support to create a test bond and to form a test structure, and bonding the test adherend to a second peeling support. A layered test coupon may be fabricated by adhering a test adherend with a test adhesive to a peeling adherend to create a test bond and to form a test structure, bonding the peeling adherend to a first peeling support, and bonding the test adherend to a second peeling support.

A layered test coupon may be fabricated by adhering a test adherend with a test adhesive to a shearing adherend to create a test bond and to form a test structure, bonding the shearing adherend to a first shearing support, and bonding the test adherend to a second shearing support.

Test coupons may comprise layers in the following sequence: (a) a base support with a first location and a second location, (b) an adhesive layer including a first test adhesive adjacent to the first location and a second test adhesive adjacent to the second location, (c) an adherend layer including a first test adherend and a second test adherend, and (d) a peeling support bonded to the first test adherend and bonded to the second test adherend. Further, the first test adherend is coupled to the first location on the base support with a first test bond including the first test adhesive, and the second test adherend is coupled to the second location on the base support with a second test bond including the second test adhesive.

Test coupons may comprise layers in the following sequence: (a) a peeling support, (b) a test adhesive, and (c) a rigid test adherend. Further, the test adherend is coupled to the peeling support with a test bond including the test adhesive.

Test coupons may comprise layers in the following sequence: (a) a peeling support, (b) a test adhesive, (c) a test adherend, and (d) a rigid base support. Further, the test adherend is coupled to the peeling support with a test bond including the test adhesive, and the base support is bonded to the test adherend.

Test coupons may comprise layers in the following sequence: (a) a test structure and (b) a second peeling support. The test structure includes layers in the following sequence: (i) a first peeling support, (ii) a test adhesive, and (iii) a test adherend. Further, the test adherend is coupled to the first peeling support with a test bond including the test adhesive, and the second peeling support is bonded to the test adherend.

Test coupons may comprise layers in the following sequence: (a) a first peeling support, (b) a test structure, and (c) a second peeling support. The test structure includes layers in the following sequence: (i) a peeling adherend, (ii) a test adhesive, and (iii) a test adherend. Further, the test adherend is coupled to the peeling adherend with a test bond including the test adhesive, the first peeling support is bonded to the peeling adherend, and the second peeling support is bonded to the test adherend.

Test coupons may comprise layers in the following sequence: (a) a first shearing support, (b) a test structure, and (c) a second shearing support. The test structure includes layers in the following sequence: (i) a shearing adherend, (ii) a test adhesive, and (iii) a test adherend. Further, the test adherend is coupled to the shearing adherend with a test bond including the test adhesive, the first shearing support is bonded to the shearing adherend, and the second shearing support is bonded to the test adherend.

The present disclosure includes methods of peel testing and/or shear testing of layered test coupons with adhesive bonds to non-metallic adherends. Testing methods may comprise peeling and/or shearing the layered test coupon, optionally followed by classifying and/or quantifying the resulting failure of the adhesive bonds.

BRIEF DESCRIPTION OF THE DRAWINGS

FIG. 2 is an illustrative, non-exclusive example of a peeling configuration.

FIG. 3 is an illustrative, non-exclusive example of a drum peeling configuration.

DESCRIPTION

Figure 1:
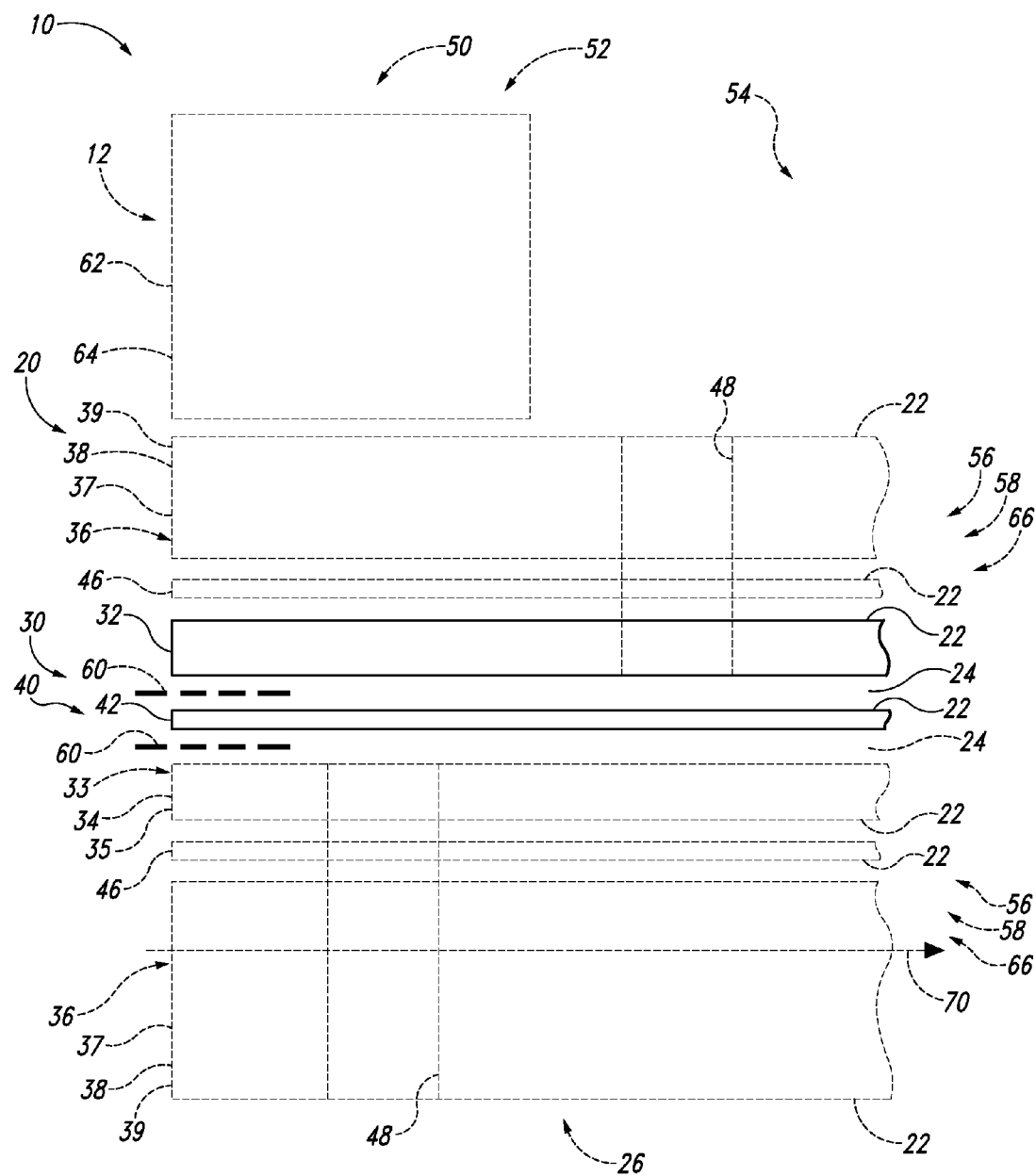
FIG. 1 is a schematic representation of test systems for rapidly testing adhesion and adhesives.

Characterization of adhesive bonds typically is performed with test coupons that include an adhesive bonding scheme, i.e., an adhesive, an adherend(s), and a bond resulting from surface preparations, adhesive cure method, and environmental conditions (e.g., heat, chemical exposure, static loading, and dynamic loading). Test coupons are layered structures that include a test adherend layer, another adherend layer, and a test adhesive layer sandwiched between the two adherend layers. The test adhesive layer is bonded to the test adherend layer to form a test bond.

Test coupons typically are tested with a test fixture configured to subject the test bond to forces that may break the test bond apart. The bond is broken by applying forces to relatively thick supports that include, and/or are bonded to, the two adherend layers. The use of thick supports provides the mechanical stability and structure required to apply testing forces. Testing typically includes peel testing and/or shear testing. For example, the test bond may be subject to peeling forces, forces that tend to pull the test bond perpendicular to the test bond layer. A test fixture configured for peel testing, i.e., configured to apply peeling forces, may be referred to as a peeling fixture. As another example, the test bond may be subject to shearing forces, forces that tend to pull the test bond parallel to the test bond layer. A test fixture configured for shear testing, i.e., configured to apply shearing forces, may be referred to as a shearing fixture.

Test methods may be qualitative and/or quantitative. Generally, qualitative test methods are rapid, yielding results that correlate with quantitative test methods. For qualitative test methods, the test bond may be characterized by the type of breakage induced by the test fixture. Further, test fixtures may be configured to characterize the type of breakage induced by the test fixture. For quantitative test methods, the test bond may be characterized by the amount of force required to break the bond and/or the amount of bond fracture caused by a given force. Further, test fixtures may be configured to measure the amount of force required to break the bond and/or the amount of bond fracture caused by a given force.

Where preparation of test coupons and/or test methods include environmental exposure (e.g., heat, chemical exposure, static loading, and dynamic loading), use of thin adherends may reduce the time of exposure required to achieve a given result (e.g., thermal equilibrium, water saturation), relative to thick adherends. Test coupons that include thin adherends also may include support structures configured for compatibility with conventional testing apparatuses.

FIGS. 1-18 illustrate various embodiments of test systems 10, test coupons 20, and methods 100 of fabricating and/or testing test systems 10 and/or test coupons 20. Elements that serve a similar, or at least substantially similar, purpose are labeled with numbers consistent among the figures. Like numbers in each of FIGS. 1-18, and the corresponding elements, may not be discussed in detail herein with reference to each of FIGS. 1-18. Similarly, all elements may not be labeled in each of FIGS. 1-18, but reference numerals associated therewith may be used for consistency. Elements, components, and/or features that are discussed with reference to one or more of FIGS. 1-18 may be included in and/or used with any of FIGS. 1-18 without departing from the scope of the present disclosure. In general, elements that are likely to be included are illustrated in solid lines, while elements that may be optional or alternatives are illustrated in dashed lines. However, elements that are shown in solid lines are not necessarily essential, and an element shown in solid lines may be omitted without departing from the scope of the present disclosure. Some figures illustrate test systems 10 and/or test coupons 20 in exploded view. In exploded view, the spaces between the elements are for illustration purposes only.

FIG. 1 is a schematic representation, in exploded view, of test systems 10 for testing bond adhesion to test adherends 32. The test system 10 comprises a test coupon 20, a layered structure including a series of layers 22 and one or more test bonds 40 to be tested. The test coupon 20 includes one or more test structures 30, layered structures that each include at least two layers 22: a test adherend 32 and a test adhesive 42. Within the test structure 30, and between the test adherend 32 and the test adhesive 42, is a test interface 24. The test adhesive 42 bonds to the test adherend 32 at the test interface 24 to form the test bond 40. The test coupon 20 includes a test region 26, sometimes referred to as a peel region or a shear region, depending on type of test performed. The test coupon 20 includes a force application region 52 where forces 50 may be applied to the test coupon 20. Depending on the type of test being performed, forces 50 may be referred to as peeling forces or shearing forces. The test region 26 is the region of the test structure 30 where the test bond 40 may be interrogated, for example by applying peeling forces (perpendicular to the layers 22) and/or shearing forces (parallel to the layers 22).

The test coupon 20 also includes a layer 22 adhered to the test adhesive 42 opposite the test adherend 32. The adhered layer 22 may be a second test adherend 32, a structural adherend 33 (e.g., a peeling adherend 34 and/or a shearing adherend 35), and/or a structural support 36 (e.g., a base support 37, a peeling support 38, and/or a shearing support 39). When present, a second test adherend 32 and/or a structural adherend 33 may be supported by a structural support 36 bonded to the second test adherend 32 and/or the structural adherend 33. Further, the test structure 30 may be supported by a structural support 36 bonded to the test adherend 32.

Generally, the test systems 10, the test coupons 20, and the test structures 30 are configured to test the quality (e.g., the strength, the durability, and/or the extent) of the test bond 40. One method to test the quality of the test bond 40 is through peel testing, where forces 50 are applied perpendicular to the layers 22 to stress the test bond 40 perpendicular to the layer 22 of the test adhesive 42. Peel testing is designed to ultimately peel apart the test coupon 20, generally by fracturing the test bond 40 along the test interface 24, within the test adherend 32 and/or within the layer 22 adhered to the test adhesive 42. In peel testing, the fracture, or crack, generally propagates perpendicular to the externally applied forces 50. Another method to test the quality of the test bond 40 is through shear testing, where forces 50 are applied parallel to the layers 22 to stress the test bond 40 parallel to the layer 22 of the test adhesive 42. Shear testing is designed to ultimately laterally pull apart the test coupon 20, generally by fracturing the test bond 40 along the test interface 24, within the test adherend 32 and/or within the layer 22 adhered to the test adhesive 42. In shear testing, the fracture, or crack, generally propagates parallel to the externally applied forces 50.

Test coupons 20 include test adherends 32 that are non-metallic (not essentially composed of metal). Test adherends 32 may be laminar and/or composite materials and may include polymeric material, plastic, glass, and/or ceramic materials. Though test adherends 32 are non-metallic, test adherends 32 may include metal as one of several components (e.g., metal fiber in a composite material) and may have metallic properties (e.g., electrically conductive). Composite materials, such as fiber-reinforced and/or mineral-filled plastic materials, include a matrix material (such as a thermoset, thermoplastic, and/or a resin), and may be reinforced with surface and/or embedded fiber and/or particulate. For example, a composite material may include a matrix material reinforced with at least one of glass fiber, carbon fiber, aramid fiber, mica, talc, and glass particulate. Generally, a laminar material, such as a fiber-reinforced plastic, is composed essentially of one or more plies cured together to form a unified structural material. The plies may be assembled (laid-up) into a variety of forms using for example, dry lay-up techniques, wet lay-up techniques, and/or prepreg techniques. Composite materials typically are cured at elevated temperatures, for example, above 100° C., above 150° C., about 120° C., about 180° C., 100° C.-200° C., and/or 150° C.-200° C.

When the test adherend 32 is a laminar material, the assembled plies of test adherend 32 may be handled and assembled onto other layers 22 while the test adherend is uncured, partially cured, and/or fully cured. In the uncured and partially cured states, the test adherend 32 may be pliable and/or malleable. Upon fully curing, the test adherend 32 may solidify and become relatively stiff and/or rigid. Some test adherends 32 may remain and/or become flexible and/or elastic in the fully cured state.

Test adherends 32 are generally thin layers 22 and, when a laminar material, typically include less than 20 plies, less than 10 plies, less than 8 plies, less than 6 plies, less than 4 plies, about 20 plies, about 10 plies, 8 plies, 6 plies, 4 plies, 3 plies, 2 plies, 1 ply, 1-20 plies, 1-8 plies, and/or 1-4 plies. In certain embodiments, test adherends 32 may be rigid and, when a laminar material, may include greater than 8 plies, greater than 10 plies, greater than 20 plies, 8-20 plies, and/or 8-40 plies.

Laminar materials may include a peel ply, e.g., a tightly woven fabric embedded near the surface of the laminar material. The peel ply is typically co-cured onto the laminar material and is configured to tear away from the bulk of the laminar material. Once the peel ply is stripped from the surface of the laminar material, the newly exposed surface is typically slightly rough and chemically active. Peel plies may include fibers such as polyester, nylon, and glass, and may be treated with release agents such as silicone and fluoropolymers.

Test coupons 20 include test adhesives 42 that are adhesives configured to bond the test adherend 32 to another layer 22. Adhesives may be referred to as binders, glues, cements, and pastes. Prior to bonding, test adhesives 42 may be in the form of a liquid, a solid, a suspension, an emulsion, and/or a mastic composition. Test adhesives 42 may be dry adhesives, pressure sensitive adhesives, contact adhesives, hot-melt adhesives, and/or reactive adhesives (e.g., epoxies, urethanes, acrylics, and polyimides), including one-part and multi-part reactive adhesives. Reactive adhesives may require application of an external stimulant such as light (e.g., UV or visible light), heat, and/or moisture. Test adhesives 42 may be room temperature cured (e.g., pressure sensitive adhesive, contact adhesive, moisture-cured adhesive), and/or heat cured. Test adhesives 42 may be cured at an elevated temperature, for example, at a temperature above 20° C., above 70° C., above 100° C., above 150° C., about 20° C., about 70° C., about 120° C., about 180° C., 20° C.-200° C., 20° C.-100° C., 100° C.-200° C., and/or 150° C.-200° C.

Test coupons 20 may include structural adherends 33 that are non-metallic (e.g., laminar components, composite components, and/or fiber-reinforced plastic components). When present, structural adherends 33 are adhered to the test adhesive 42 opposite the test adherend 32. When present, structural adherends 33 form a part of the test structure 30. Structural adherends 33 may have any of the properties disclosed herein with respect to test adherends 32. Structural adherends 33 may be configured similarly or identically to a test adherends 32 in the same test structure 30. For example, a structural adherend 33 may be selected to cure under the same conditions as a test adherend 32 in the same test structure 30. In certain embodiments, the structural adherend 33 is substantially the same as the test adherend 32. In certain other embodiments, the structural adherend 33 is configured to adhere more strongly to the test adhesive 42 than the adhesion of the test adherend 32 to the test adhesive 42. The structural adherend 33 may be configured to be thin, and may be configured to have substantially the same thickness as the test adherend 32.

Where the test system 10, the test coupon 20, and/or the structural adherend 33 are configured for peel testing, the structural adherend 33 may be referred to as a peeling adherend 34. The peeling adherend 34 may be configured to transmit peeling stress to the test bond 40 and may be configured to avoid shearing while peeling forces are applied. The peeling adherend 34 may be configured to be flexible, optionally as flexible as the test adherend 32.

Where the test system 10, the test coupon 20, and/or the structural adherend 33 are configured for shear testing, the structural adherend 33 may be referred to as a shearing adherend 35. The shearing adherend 35 may be configured to transmit shearing stress to the test bond 40 and may be configured to avoid peeling while shearing forces are applied.

Test coupons 20 may include structural supports 36, sometimes referred to as a base support 37, a peeling support 38, and/or a shearing support 39 depending on how forces 50 are configured to be applied to the test coupon 20. Structural supports 36 are generally rigid structures configured to supply mechanical strength to the test coupon 20. Further, structural supports 36 are configured to bond strongly to at least one layer 22 of the test structure 30, for example the test adherend 32, the test adhesive 42, and the structural adherend 33. Structural supports 36 may include, and may consist essentially of, at least one of metal, aluminum alloy, and steel. Further, structural supports 36 may include, and may consist essentially of, at least one of polymeric material, plastic, laminar material (e.g., fiber-reinforced plastic), composite material, glass, and ceramic.

Where the test system 10 and/or the test coupon 20 are configured for peel testing, a base support 37 may be bonded to the test adherend 32, test adhesive 42, and/or the optional peeling adherend 34. In such case, the base support 37 would form a stable reference from which other layers 22 could be peeled. Where the test system 10 and/or the test coupon 20 are configured for shear testing, a shearing support 39 may be bonded to the test adherend 32, test adhesive 42, and/or the optional shearing adherend 35. In the case of shear testing, a first shearing support 139 (a shearing support 39) may be bonded to the shearing adherend 35 and a second shearing support 239 (a shearing support 39) may be bonded to the test adherend 32.

Test coupons 20 may include peeling supports 38 that are support structures configured to supply mechanical strength to the test coupon 20 and to transmit peeling stress to the test bond 40 (through the test adherend 32 and/or the peeling adherend 34). Peeling supports 38 may be configured to avoid shearing while peeling forces are applied. Further, peeling supports 38 are configured to bond strongly to at least one layer 22 of the test structure 30, for example the test adherend 32, the test adhesive 42, and the peeling adherend 34. The peeling support 38 may be configured to be relatively flexible, optionally as flexible as the test adherend 32 and/or the peeling adherend 34. Peeling supports 38 may include, and may consist essentially of, at least one of metal, aluminum alloy, and steel.

Where test coupons 20 include an optional structural support 36, the structural support 36 may be bonded to the test structure 30 (i.e., the test adherend 32 and/or a structural adherend 33) with a structural adhesive 46. Structural adhesives 46 are adhesives configured to strongly bond the structural support 36 to the test structure 30. Structural adhesives 46 may have any of the properties disclosed herein with respect to test adhesives 42 and adhesives generally. Structural adhesives 46 may be configured similarly or identically to a test adhesive 42 in the same test coupon 20. For example, a structural adhesive 46 may be selected to cure under the same conditions as a test adhesive 42 in the same test coupon 20.

Additionally or alternatively, the optional structural support 36 may be directly bonded to the test structure 30, without any structural adhesive 46. For example, the test adherend 32 and/or a structural adherend 33 may be cured while assembled on a structural support 36, the curing process forming a bond between the test structure 30 and the structural support 36.

Overall, test coupons 20 generally include layers 22 in the following sequence: (a) an optional structural support 36, (b) an optional structural adhesive 46, (c) a test adherend 32 (a first test adherend 132), (d) a test adhesive 42, (e) an optional second test adherend 232 (a test adherend 32) and/or an optional structural adherend 33, (f) an optional structural adhesive 46, and (g) an optional structural support 36. As discussed herein, test coupons 20 include at least one test structure 30 which includes a test adherend 32, a test adhesive 42 and at least one of optional layers (e) and (g). Hence, test coupons 20 include at least one of optional layers (e) and (g).

In certain embodiments, test coupons 20 may include a crack starter 60 in the test structure 30, at the edge of the test interface 24 between the test adherend 32 and the test adhesive 42. The crack starter 60 is configured to form a weak bond, and/or to interfere with the formation of a strong bond, along a portion of the test interface 24, typically in the force application region 52. The crack starter 60 also is configured to form a crack in the test bond 40, near the test interface 24, upon application of a force 50 near the crack starter 60. The crack starter 60 may be a solid, liquid, and/or mastic applied at the edge of the test interface 24. Illustrative, non-exclusive example materials suitable for a crack starter 60 include FEP (fluorinated ethylene propylene), PTFE (polytetrafluoroethylene), polyimide, mold release agents, and silicone.

In certain embodiments, test coupons 20 may include one or more gaps 48 that define a test region 26 (e.g., between the gaps 48). The optional gaps 48 are discontinuities crossing certain layers 22 but do not intersect the test adhesive 42. For example, a gap 48 may intersect the optional structural support 36 and/or the optional peeling support 38, the optional structural adhesive 46, and the test adherend 32, leaving intact the test adhesive 42, the optional second test adherend 32 and/or the optional structural adherend 33, the optional structural adhesive 46, and the optional structural support 36. When test coupons 20 include gaps 48, typically two are included. The two gaps are typically spaced apart from one another and situated on opposite sides of the test coupon 20 (opposite sides of the test adhesive 42). The layers between the gaps 48 are generally intact. Typically, the gaps 48 define a test region 26 where the optional structural supports 36 on either side of the test adhesive 42 overlap one another. Such an overlap structure may be useful for shear testing (e.g., pulling oppositely situated structural supports 36 in opposite directions may subject the test bond 40 to shear stress).

Test systems 10 may include a test fixture 12 configured to apply forces 50 to the test coupon 20 and the test bond 40. For example, a test fixture 12 may be configured for peel testing, i.e., configured to apply forces 50 perpendicular to the layers 22 to stress the test bond 40 perpendicular to the layer 22 of the test adhesive 42. As another example, a test fixture 12 may be configured for shear testing, i.e., configured to apply forces 50 parallel to the layers 22 to stress the test bond 40 parallel to the layer 22 of the test adhesive 42. The test fixture 12 generally is configured to apply forces 50 to the structural supports 36 and/or the peeling supports 38, as the structural supports 36 and/or the peeling supports 38 generally are configured to accept and transmit forces 50. Test fixtures 12 may include a motor, an actuator, and/or a simple machine (e.g., a lever, a plane, a wedge 64, and/or a drum 62).

Generally, the test fixture 12 is configured to apply forces 50 to the test coupon 20 at one or more force application regions 52 and to maintain the relative position of the test coupon 20 at one or more stationary regions 54. Generally, the force application regions 52 are located near an end of the test coupon 20. The test fixture 12 may be coupled to the test coupon 20 at the force application regions 52 with flexible couplings that allow the force 50 to be applied at a substantially constant direction as the test coupon 20 is split apart. The test fixture 12 may be coupled to the test coupon 20 at the stationary regions 54 with rigid couplings that substantially maintain the relative position of the stationary regions 54 as the test coupon 20 is split apart. In certain configurations, the test fixture 12 is not coupled directly to the stationary regions 54.

Figure 4:
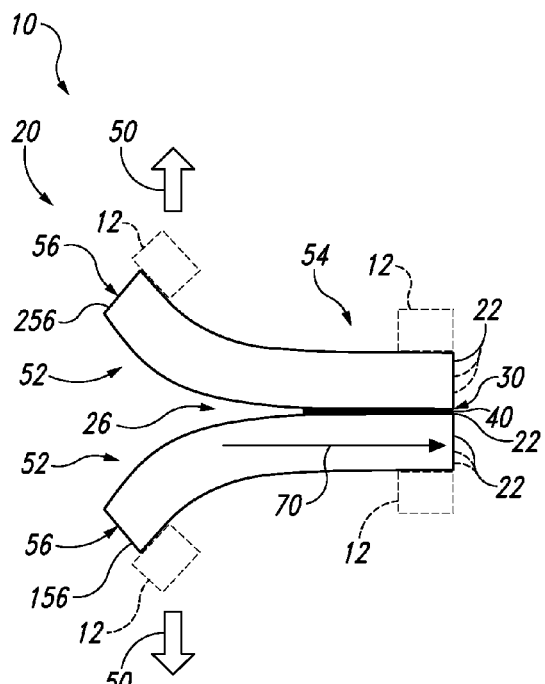
FIG. 4 is an illustrative, non-exclusive example of a double cantilever peeling configuration.
Figure 5:
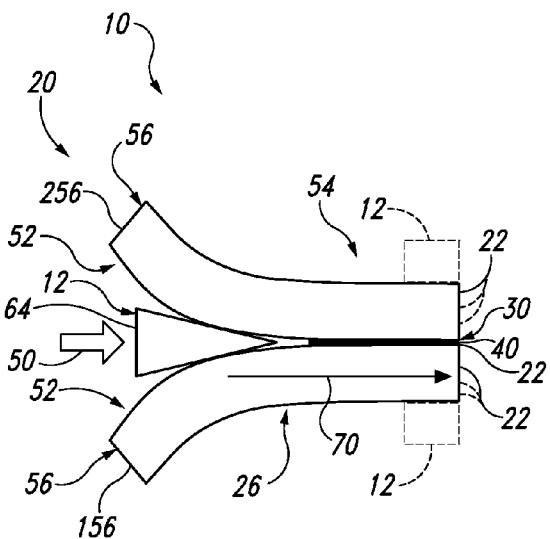
FIG. 5 is an illustrative, non-exclusive example of a wedge peeling configuration.
Figure 6:
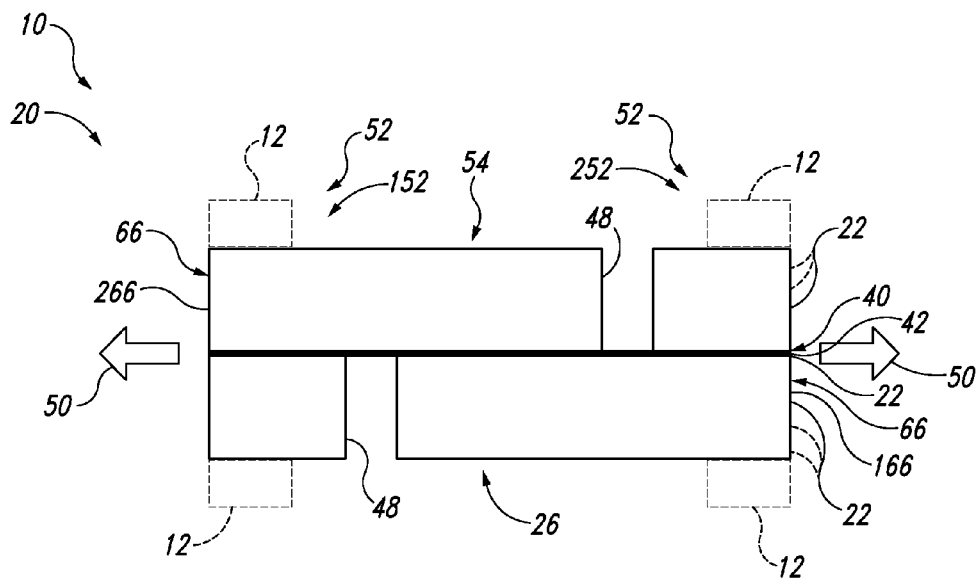
FIG. 6 is an illustrative, non-exclusive example of a shearing configuration.

Test systems 10 and/or test fixtures 12 may be configured to interrogate test bonds 40 within test coupons 20 in at least one of several modes, as illustrated in FIGS. 2-6. In peeling mode, as illustrated in FIGS. 2-5, the test bond 40 is subject to forces 50, perpendicular to the test structure 30 layer 22 (including the test adhesive 42 layer 22), that tend to peel the test bond 40 apart. In shearing mode, as illustrated in FIG. 6, the test bond 40 is subject to forces 50, parallel to the test adhesive 42 layer 22, that tend to shear the test bond 40 apart.

In FIG. 2, a test coupon 20 is subject to peel testing. One side of the test coupon 20 (the backing structure 58) is rigidly coupled to a rigid portion of a test fixture 12 (or is rigid enough to serve as a rigid fixture support) while one end (the force application region 52) of a peeling structure 56 (the side of the test coupon 20 opposite the backing structure 58) is coupled to a peeling mechanism of the test fixture 12. The backing structure 58 may include and/or be the test adherend 32, the structural adherend 33, and/or the base support 37. The peeling structure 56 may include and/or be the structural adherend 33, the test adherend 32, and/or the peeling support 38. The test fixture 12 is configured to pull the test coupon 20 apart between the backing structure 58 and the peeling structure 56 (generally at the test bond 40). The peeling force 50 may be applied at an angle to the layer 22 of the test structure 30, generally substantially perpendicular to the layer 22 of the test structure 30, at least not essentially parallel to the layer 22 of the test structure 30 (as parallel forces would result in more shearing than peeling).

Generally, the peeling structure 56 must be flexible enough to bend as the test coupon 20 is pulled apart and stiff enough to transmit the peeling force 50 of the test fixture 12 into the test bond 40. Typically, the peeling structure 56 includes a thin, metal layer 22 (e.g., the peeling support 38). The peeling structure 56 may be coupled to the test fixture 12 with fasteners and/or bonds. For example, the force application region 52 of the peeling structure 56 may be clamped to the test fixture 12. The backing structure 58 may be stiff and rigid enough to withstand the peeling forces 50 without significant flexing. Additionally or alternatively, the backing structure 58 may be coupled to a rigid portion of the test fixture 12 such that the combination of the rigid portion and the backing structure 58 is stiff and rigid enough to resist significant flexing as the peeling forces 50 are applied. The backing structure 58 may be coupled to the test fixture 12 with fasteners and/or bonds. For example, the backing structure 58 may be clamped to the test fixture 12.

In FIG. 3, the test fixture 12 illustrated in FIG. 2 includes a drum 62. The drum 62 (i.e., a cylindrical structure) is configured to be coupled to the peeling structure 56. The drum 62 also is configured to roll along the test coupon 20, pulling the test coupon 20 apart between the backing structure 58 and the peeling structure 56 (generally at the test bond 40). The general procedure and apparatus for metal to metal bond testing are described in ASTM D1781 (ASTM International), herein incorporated by reference. Generally, the peeling structure 56 must be flexible enough to conform to the drum 62 as the drum 62 rolls. The peeling structure 56 may be coupled to the drum 62 with fasteners and/or bonds. For example, the force application region 52 of the peeling structure 56 may be clamped to the drum 62. Incorporating a drum 62 is one way to configure a test fixture 12 to control the peeling angle (the angle between the peeling structure 56 and the backing structure 58) as the peeling structure 56 is peeled from the backing structure 58. Peeling the peeling structure 56 by rolling around a drum 62 may maintain a substantially constant peeling angle.

In FIG. 4, a test coupon 20 is subject to peel testing in a double beam cantilever configuration. One end (the force application region 52) of one side of a test coupon 20 (the first peeling structure 156, a peeling structure 56) is coupled to a pulling mechanism of a test fixture 12 while the same end (the force application region 52) of the second peeling structure 256 (a peeling structure 56 that is the side of the test coupon 20 opposite the first peeling structure 156) is coupled to a second pulling mechanism of the test fixture 12. The first peeling structure 156 may include and/or be the test adherend 32 and/or a first peeling support 138. The second peeling structure 256 may include and/or be the peeling adherend 34 and/or a second peeling support 238. The test fixture 12 is configured to pull the end of the first peeling structure 156 and the end of the second peeling structure 256 with substantially equal magnitude forces 50 in generally opposite directions, the forces 50 tending to pull the test bond 40 apart perpendicular to the layer 22 of the test structure 30. The general procedure and apparatus for double cantilever beam peel testing for composite material failure (not bond failure) are described in ASTM D5528 (ASTM International), herein incorporated by reference. Typically, the ends of the peeling structures 56 are coupled to form a link between two cables, or other flexible pulling elements. In that case, as the cable (or other flexible pulling element) is pulled, the test bond 40 is subject to the tension of the cable (or other flexible pulling element). The ends of the peeling structures 56 may be coupled to the pulling mechanisms with fasteners and/or bonds. For example, a hinge coupled to a pulling mechanism may be bonded to the end of one of the peeling structures 56. As another example, the end of one of the peeling structures 56 may include a hole configured to receive a hook coupled to a pulling mechanism.

In FIG. 5, a test coupon 20 is subject to peel testing in a double beam cantilever configuration using a wedge 64 (part of the test fixture 12). The test fixture 12 may be configured to drive the wedge 64 along the test bond 40 (along the peeling direction 70) to separate the test coupon 20 along the test bond 40. In this configuration, the wedge 64 is placed with its tip at the test structure 30. The wedge 64 may be driven by a mechanical device such as a hydraulic press and/or a threaded mechanism, and may be driven by a series of impacts, e.g., by the operator hitting the wedge 64. The test coupon 20 may be coupled to the test fixture 12 at the end opposite the wedge 64 (at the stationary region 54), using fasteners and/or bonds. The end where the wedge will be driven (the force application region 52) need not be substantially constrained. The test fixture 12 may be configured to allow the force application region 52 to flex enough to accommodate the wedge 64 as it is driven through the test coupon 20.

In FIG. 6, a test coupon 20 is subject to shear testing. One end of a test coupon 20 (a first force application region 152) is coupled to a pulling mechanism of a test fixture 12 while the other end of the test coupon 20 (a second force application region 252) is coupled to a second pulling mechanism of the test fixture 12. The test fixture 12 is configured to apply to the test coupon 20 substantially equal magnitude pulling forces 50 in opposite directions, substantially parallel to the test adhesive 42 layer 22. The test coupon 20 includes a test region 26 where a first shearing structure 166 (a shearing structure 66) overlaps a second shearing structure 266 (a shearing structure 66), however neither shearing structure 66 is continuous from end to end of the test coupon 20. Each shearing structure 66 may include and/or be a test adherend 32, a structural adherend 33, and/or a shearing support 39. Each shearing structure 66 includes at least one gap 48 between the ends of the test coupon 20. Hence, when the force 50 is applied at the force application regions 52, to pull the test coupon 20 in opposite directions, the test adhesive 42 experiences a shear (a force parallel to the test adhesive 42 layer 22), the test adhesive 42 being the only continuous layer of the test coupon 20 between the two ends of the test coupon 20. The general procedure and apparatus for bond shear testing are described in ASTM D3165 (ASTM International), herein incorporated by reference. The ends of the test coupon 20 may be coupled to the test fixture 12 with fasteners and/or bonds. For example, a force application region 52 may define an aperture through the test coupon 20, which is configured to couple to a cable. As another example, a force application region 52 may be clamped to a pulling mechanism of the test fixture 12.

Figure 7:
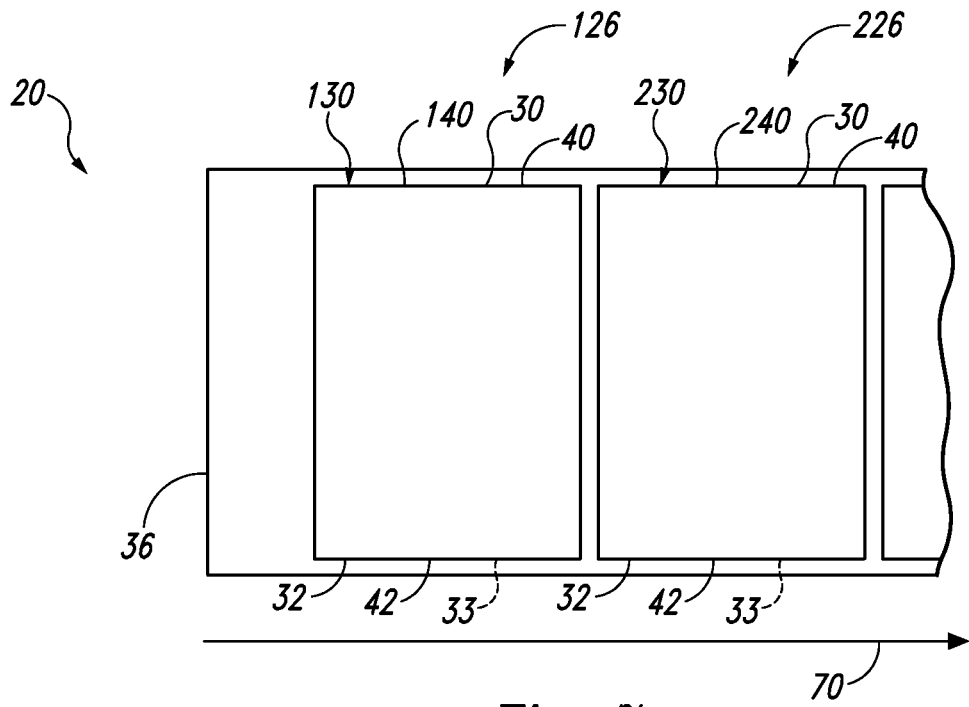
FIG. 7 is an illustrative, non-exclusive example of a series of test structures in a test coupon.
Figure 8:
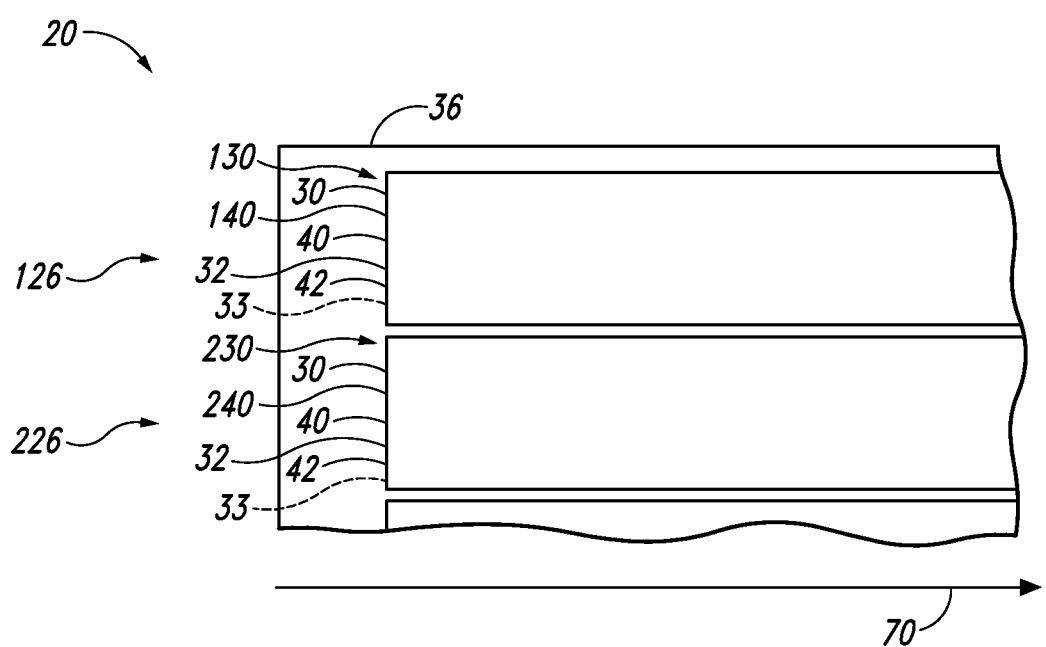
FIG. 8 is another illustrative, non-exclusive example of a series of test structures in a test coupon.

As illustrated in the fragmentary views of FIGS. 7-8, test coupons 20 may include a plurality of test bonds 30 resulting from a plurality of adhesive bonding schemes, e.g., different test adherends 32, different test adhesives 42, different preparations, and/or different environmental conditions. For example, test coupons 20 may incorporate more than one test structure 30. Each test structure 30 may be completely independent or some test structures 30 may share common materials (e.g., test adherends 32, test adhesives 42, and/or structural adherends 33) and/or bond processing conditions (e.g., surface preparations, adhesive cure methods, and environmental conditions). A test coupon 20 may include a first test structure 130 (a test structure 30) at a first location (e.g., a first test region 126) and a second test structure 230 (a test structure 30) at a second location (e.g., a second test region 226) spaced apart from the first location. Each test structure 30 includes a test bond 40 (e.g., a first test bond 140 in the first test structure 130 and a second test bond 240 in the second test structure 230). Where test adherends 32 differ between test bonds 40, the difference may be the result of different materials, different surface preparations, and/or exposure to different environmental conditions. Where the test adhesives 42 differ between test bonds 40, the difference may be the result of different materials, different adhesive cure methods, and/or exposure to different environmental conditions. When plural test structures 30 are present, they are arranged in the same layer 22 of the test coupon 20. Hence, a test fixture 12 may be configured to sequentially and/or concurrently test the quality of the test bonds 40 within the plural test structures 30. FIG. 7 illustrates a series of test structures 30 arranged such that peeling along the peeling direction 70 would sequentially interrogate each test structure 30. FIG. 8 illustrates a series of test structures 30 arranged such that peeling along the peeling direction 70 would simultaneously interrogate each test structure 30.

Figure 9:
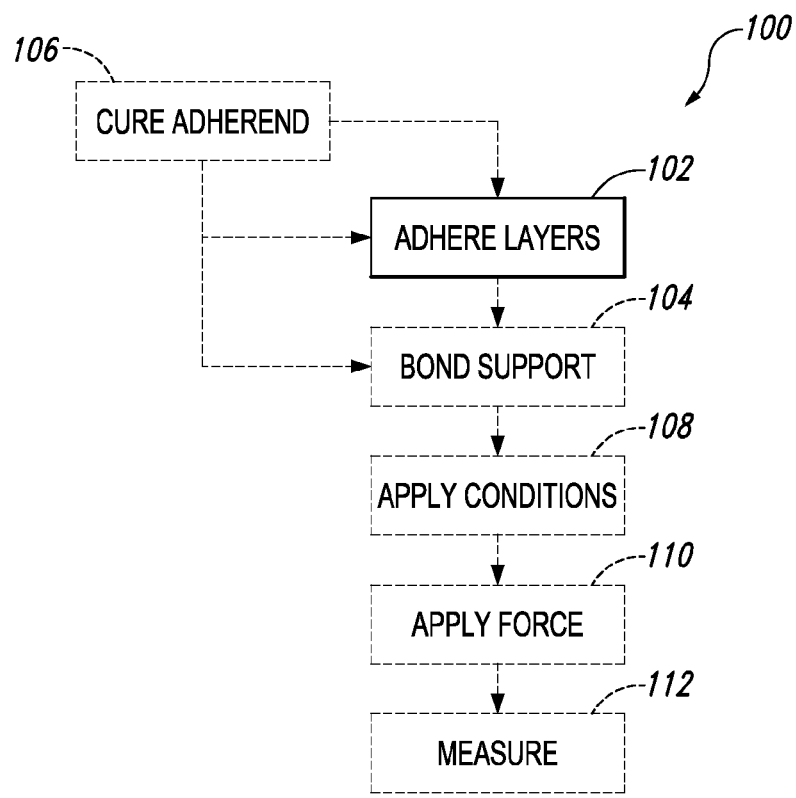
FIG. 9 is a flowchart of methods of fabricating test coupons and interrogating bonds.

FIG. 9 is a flowchart of methods 100 for fabricating test coupons 20 and/or interrogating test bonds 40. Methods 100 include adhering 102 layers 22 together to form a test structure 30. Adhering 102 includes adhering a test adherend 32 with a test adhesive 42 to an opposing adherend (e.g., a structural adherend 33 and/or a structural support 36) to create a test bond 40. Adhering 102 may include applying the test adhesive 42 between the test adherend 32 and the opposing adherend, e.g., by spraying, painting, spreading, placing, and/or contacting. Adhering 102 may include curing the test adhesive 42. Curing may include heating, cooling, compressing, and/or applying an external stimulant (such as light, e.g., UV or visible light, and/or moisture). Curing may include curing at a temperature above 20° C., above 70° C., above 100° C., above 150° C., about 20° C., about 70° C., about 120° C., about 180° C., 20° C.-200° C., 20° C.-100° C., 100° C.-200° C., and/or 150° C.-200° C. Further, adhering 102 may include preparing the surface of test adherend 32 to be adhered. The prepared surface may become part of the test interface 24. For example, preparing may include peeling a peel ply, priming, cleaning (e.g., wiping with solvent), contaminating, sanding, and/or grit blasting. Preparing may be selected to affect the test bond 40 and may be one of the variables interrogated with the test structure 30 and/or the test coupon 20. For example, where the test adherend 32 includes a peel ply, the peel ply may be removed from the surface of the test adherend 32, exposing a fresh surface for the test interface 24.

Methods 100 may include adhering 102 layers 22 to form a plurality of test structures 30. Each test structure 30 may be in a different location and spaced apart from other test structures 30. The test structures 30 may share a common test adherend 32, a common test adhesive 42, and/or a common opposing adherend. For example, adhering 102 may include adhering a first test adherend 32 with a first test adhesive 42 to a first location on an opposing adherend to create a first test bond 40, and include adhering a second test adherend 32 with a second test adhesive 42 to a second location, adjacent the first location, on the opposing adherend to create a second test bond 40. Adhering 102 may be performed such that one of the plurality of test structures 30 is formed at least partially concurrently and/or at least partially sequentially with another of the plurality of test structures 30. Where adhering 102 includes curing the test adhesive(s) 42, curing each test adhesive 42 of the plurality of test structures 30 may be performed under substantially the same conditions (e.g., temperature, time, application method, etc.).

Methods 100 may include bonding 104 the test structure 30 to one or more supports (e.g., a structural support 36). Bonding 104 may include bonding a first support on one side of the test structure 30 (e.g., bonding a peeling support 38 to a test adherend 32) and/or bonding a second support on the opposite side of the test structure 30 (e.g., bonding a base support 37 to a structural adherend 33). Bonding 104 may include curing a composite material. Curing a composite material may bond the composite material to other materials in contact. For example, where bonding 104 includes bonding the test adherend 32 (potentially a laminar and/or composite material) to a structural support 36 (potentially a laminar and/or a composite material), bonding 104 may include curing the test adherend 32 and/or the structural support 36 in contact with each other. Bonding 104 may include applying a structural adhesive 46 between the support (e.g., the structural support 36) and the test structure 30, and optionally may include curing the structural adhesive 46 to bond the two components. Bonding 104 may be performed at least partially concurrently and/or at least partially sequentially with adhering 102. For example, where adhering 102 includes curing the test adhesive 42, bonding 104 may include curing a composite material at least partially concurrently with the curing of the test adhesive 42, e.g., the curing of the test adhesive 42 and the curing of the composite material may occur under similar conditions (such as time, temperature, humidity, etc.). Where methods 100 include two or more bonding 104 operations, e.g., bonding a structural support 36 to a structural adherend 33 and bonding a peeling support 38 to the test adherend 32, one bonding 104 may be performed at least partially concurrently and/or partially sequentially with another bonding 104. For example, bonding 104 a structural support 36 to a structural adherend 33 and bonding 104 a peeling support 38 to the test adherend 32 may be performed at least partially concurrently, e.g., the two bonding operations may occur under similar conditions (such as time, temperature, humidity, etc.). Where methods 100 include adhering 102 to form a plurality of test structures 30, bonding 104 may include bonding each test structure 30 to one or more common supports (e.g., a structural support 36 and/or a peeling support 38).

Methods 100 may include curing 106 composite structures such as the test adherend 32, the structural adherend 33, the structural support 36, and/or the peeling support 38. Composite structures may be assembled in an uncured or partially cured state (a green state). For example, prepreg composites require a final curing step to harden the matrix and form the final material. Any test adherend 32, any support adherend 33, and/or any structural support 36 including composite materials may be assembled in a green state. After assembly of the test structure 30 and/or the test coupon 20, the green composite material may be cured, typically by heating the whole assembly to the curing temperature of the green composite material. Curing 106 of the green composite material generally results in bonding the green composite material to the adjacent layers 22. Where the test adhesive 42 and/or the structural adhesive 46 requires curing at an elevated temperature, the green composite material and the adhesive may be cured at the same time by subjecting the assembly to the elevated temperature. Additionally or alternatively, any composite material may be fully cured before assembly into the test structure 30 and/or the test coupon 20. Curing 106 may include heating the composite structure to a temperature of above 100° C., above 150° C., about 120° C., about 180° C., 100° C.-200° C., and/or 150° C.-200° C. Curing 106 of a composite structure may be before, during, or after adhering 102. Curing 106 of a composite structure may be before or during bonding 104. For example, curing 106 the test adherend 32 and curing the test adhesive 42 (as part of adhering 102) may be performed at least partially concurrently and/or at least partially sequentially. Where methods 100 include two or curing 106 operations, one curing 106 operation may be performed at least partially concurrently and/or partially sequentially with another curing 106 operation. For example, curing 106 the test adherend 32 and curing 106 a structural adherend 33 may be performed at least partially concurrently, e.g., the two curing operations may occur under similar conditions (such as time, temperature, humidity, etc.).

Methods 100 may include fabricating composite structures such as the test adherend 32, the structural adherend 33, and/or the structural support 36. Fabricating may include assembling laminar materials and/or composite materials (e.g., assembling the matrix material and the fiber of a fiber-reinforced plastic). Fabricating may include dry lay-up techniques, wet lay-up techniques, and/or prepreg techniques. Fabricating may include assembling plies of fiber and may include assembling less than 20 plies, less than 10 plies, less than 8 plies, less than 6 plies, less than 4 plies, about 20 plies, about 10 plies, 8 plies, 6 plies, 4 plies, 3 plies, 2 plies, 1 ply, greater than 8 plies, greater than 10 plies, greater than 20 plies, 1-20 plies, 1-8 plies, 1-4 plies, 8-20 plies, and/or 8-40 plies.

Methods 100 may include forming a crack initiation site at the test bond 40 in the force application region 52. For example, forming a crack initiation site may include placing a crack starter 60 between a portion of the test adherend 32 and the test adhesive 42 before adhering 102. As another example, forming a crack initiation site may include placing a crack starter 60 between a portion of the structural adherend 33 and the test adhesive 42 before adhering 102. Placing the crack starter may include applying a crack starter 60 to the test adherend 32. As another example, forming a crack initiation site may include forming a weak bond between a portion of the test adherend 32 and the test adhesive 42. As another example, forming a crack initiation site may include initiating a crack in the test bond 40 in the force application region 52, e.g., by driving a wedge into the test bond 40, applying a wedge between layers 22 of the test structure 30, and/or by applying a force 50. Where methods 100 include forming a plurality of test structures 30, methods 100 may include forming a crack initiation site in each test structure 30.

Methods 100 may include applying 108 test conditions to the test structure 30 prior to bonding 104. Test structures 30 may be exposed to environmental conditions (e.g., heat, chemical exposure, static loading, and dynamic loading) to investigate the effects of such conditions on the test bond 40. Exposure may include moisture, liquids, elevated temperatures, depressed temperatures, temperature cycles, corrosives, and ambient conditions for a predetermined amount of time. Applying 108 test conditions may include wetting, aging, and/or heating a test structure 30. Conditions may be applied for a period of time, for example, less than 100 days, less than 50 days, less than 20 days, less than 15 days, less than 10 days, less than 200 hours, less than 150 hours, less than 100 hours, at least 48 hours, at least 72 hours, at least 100 hours, at least 150 hours, at least 200 hours, at least 10 days, 48 hours-100 days, 48 hours-20 days, and/or 100 hours-20 days. Thinner and/or lower volume test structures 30 generally respond to condition effects quicker than thicker and/or higher volume test structures 30. Hence, steady state (quasi-equilibrium) effects may be observed sooner in thinner and/or lower volume test structures 30 than in thicker and/or higher volume test structures 30. For example, water saturation of a test structure 30 including a fiber-reinforced plastic test adherend 32 of 2 plies may occur in less than 20 days, whereas a test structure 30 differing only by including a test adherend of 10 plies may require more than 200 days for saturation. Additionally or alternatively, thinner and/or lower volume test structures 30 may reduce preparation time and materials cost relative to thicker and/or higher volume test structures 30.

Methods 100 may include forming a gap 48 through a shearing structure 66, and/or through shearing structures 66 on opposite sides of a test coupon 20, to define a test region 26 where all layers 22 of the test coupon 20 are intact. Forming a gap 48 may include cutting, notching, and/or nicking a shearing structure 66. Forming a gap 48 may include bonding discontinuous sections of a support structure (e.g., a structural support 36) to the test structure 30 and cutting, notching, and/or nicking the test structure 30 in a location corresponding to the discontinuity in the support structure. Forming a gap 48 does not generally include affecting the test adhesive 42, at least not within the test region 26. Forming a gap 48 may be performed before, during, or after applying 108 test conditions.

Methods 100 may include selecting a test coupon 20 fabricated by adhering 102, optional bonding 104, and/or optional curing 106. Test coupons 20 selected and/or fabricated according to the present disclosure may be tested. For example, the quality (including the strength, the durability, and/or the extent) of test bonds 40 may be tested by applying 110 force and optionally measuring 112 the result.

Methods 100 may include applying 110 force to the test coupon 20, the test structure 30, and/or the test bond 40 to separate the test coupon 20, generally along the test bond 40. Applying 110 force may be used to test the quality of the test bond 40. Where test coupons 20 include a plurality of test structures 30 and test bonds 40, applying 110 force may include applying 110 force to each of the plurality of test structures 30 and/or test bonds 40 at least partially concurrently and/or at least partially sequentially. Applying 110 force may include applying a force 50 to a test structure 30 and/or a test bond 40 and applying a different force 50 to a different test structure 30 and/or a different test bond 40.

Applying 110 force may include peeling one side (e.g., the test adherend 32, the structural support 36, and/or the peeling support 38) of the test coupon 20 from the other side (e.g., the structural adherend 33, and/or the structural support 36), generally by applying forces 50 perpendicular to the layers 22. Peeling may stress the test bond 40 perpendicular to the layer 22 of the test adhesive 42. Peeling may fracture the test bond 40 along the test interface 24, within the test adherend 32 and/or within the layer 22 adhered to the test adhesive 42. Peeling may include controlling the angle of the peeling support 38 relative to the base support 37 as the peeling support 38 separates from the base support 37, e.g., by using a drum peel technique. Where test coupons 20 include a plurality of test structures 30 and test bonds 40, peeling may include partially peeling the peeling support 38 from a structural support 36 to test one test bond 40 and partially peeling the peeling support 38 from the structural support 36 to test a different test bond 40.

Applying 110 force may include shearing one end (e.g., a first force application region 52) of the test coupon 20 from another end (e.g., a second force application region 52), generally by applying forces 50 parallel to the layers 22. Shearing may stress the test bond 40 parallel to the layer 22 of the test adhesive 42. Shearing may fracture the test bond 40 along the test interface 24, within the test adherend 32 and/or within the layer 22 adhered to the test adhesive 42.

Figure 10:
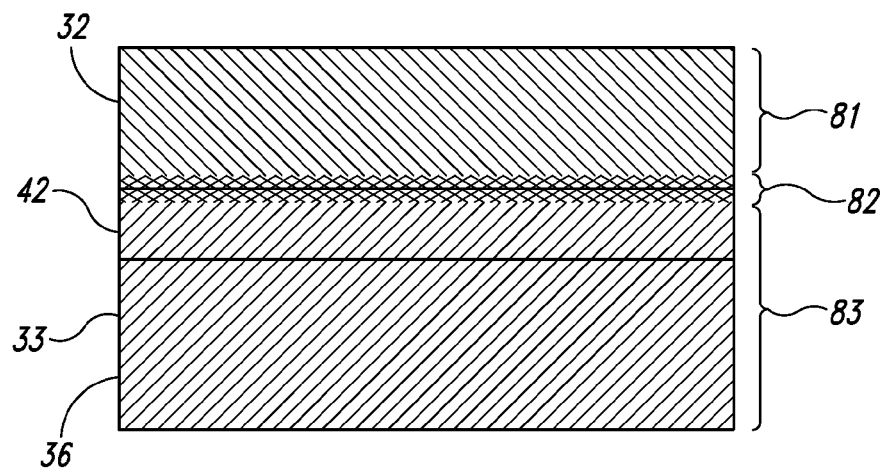
FIG. 10 is a schematic representation of the location of failure zones within illustrative, non-exclusive examples of test structures.

Methods 100 may include measuring 112 the result of applying 110 force. Measuring 112 may include classifying the failure mode of a test bond 40 after the force 50 has broken the test bond 40 (resulting in a split test coupon 20). Classifying may include observing the bond residue on the split test coupon 20, optionally observing by electronic imaging. As illustrated in FIG. 10, generally, a test bond 40 may fail at a laminal failure zone 81, an interfacial failure zone 82, and/or a cohesion failure zone 83. Hence, failure modes may be classified as laminal failure, interfacial failure, cohesion failure, and/or some combination of these failure modes. Failure at the interfacial failure zone 82, the zone at the test interface 24, between the test adherend 32 and the test adhesive 42, generally is indicative of a weak bond. Strong bonds generally result in failures at the laminal failure zone 81, the zone within the (potentially laminar) test adherend 32, and at the cohesion failure zone 83, the zone within the test adhesive 42, the structural adherend 33, and/or the structural support 36. In failure at the laminal failure zone 81, the test bond 40 remains intact yet the test adherend 32 separates within and/or between the adherend plies. In failure at the cohesion failure zone 83, the test bond 30 also remains intact. Instead, at least one of the test adhesive 42, the structural adherend 33, and the structural support 36 separates.

Measuring 112 may include quantifying the extent of failure of the test bond 40 after the force 50 has broken the test bond 40 (resulting in a split test coupon 20). Quantifying may include observing the bond residue on the split test coupon 20 by electronic imaging. Quantifying may include determining at least one of a fraction of laminal failure, a fraction of interfacial failure, a fraction of cohesion failure, an extent of laminal failure, an extent of interfacial failure, and an extent of cohesion failure. Where a test coupon 20 includes a plurality of test structures 30 and/or test bonds 40, measuring 112 may include comparing the classification, fraction and/or extent of failure between at least two of the test bonds 40.

Figure 11:
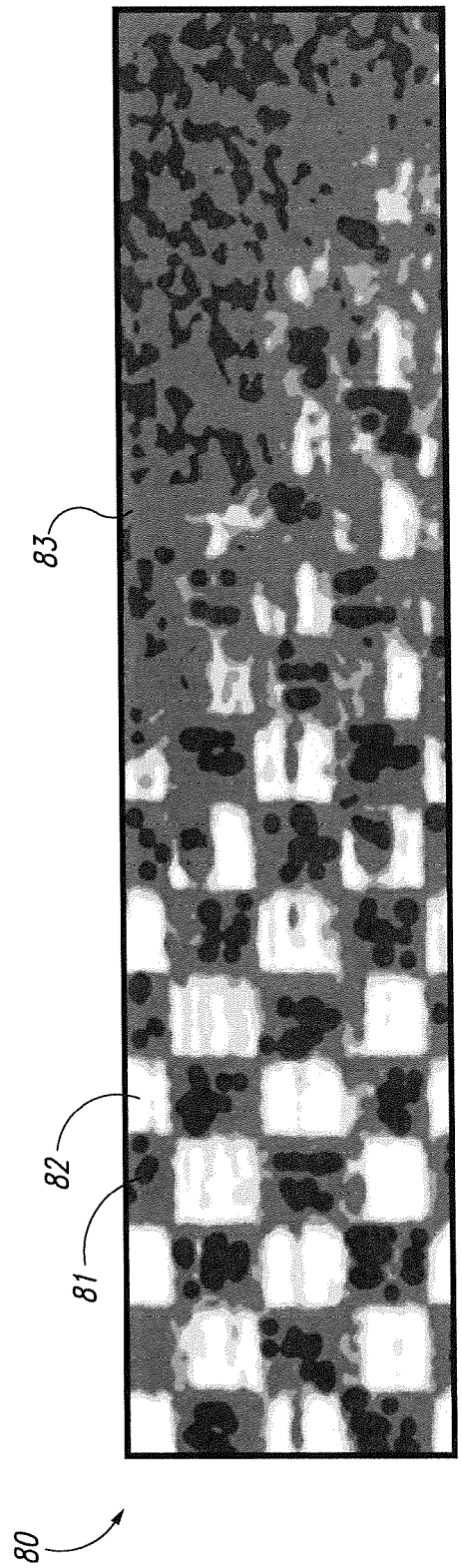
FIG. 11 is an image of a test structure after peeling.
Figure 12:
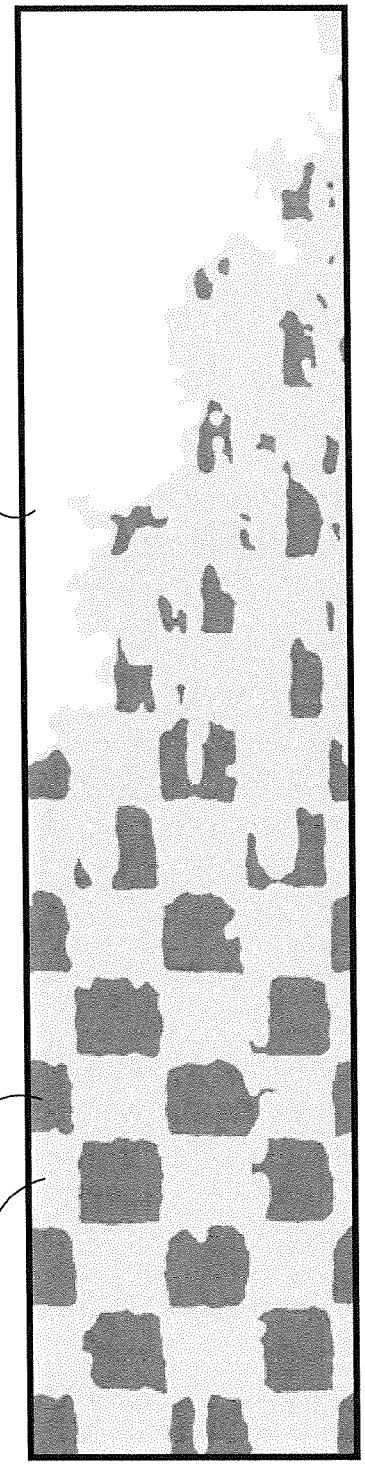
FIG. 12 is a representation of various failure regions of the test structure shown in FIG. 11.

The extent (the total area of failure) and the fraction of failure may be quantified by processing images 80 of the split test coupon 20, as illustrated in FIG. 11. Image 80 of FIG. 11 shows the residue of three failure modes: failure at the laminal failure zone 81, failure at the interfacial failure zone 82, and failure at the cohesion failure zone 83. Each failure zone may leave a distinctive imprint and/or residue on the split test coupon 20. For example, failure at the laminal failure zone 81 may leave an imprint and/or residue of the plies of the test adherend 32, generally a broad repeating texture. Failure at the interfacial failure zone 82 may leave an imprint and/or residue of surface contour of the test adherend 32, e.g., when the test adherend 32 is prepared by peeling a peel ply, the test adherend 32 surface has an imprint of the removed peel ply, a tightly woven texture. Failure at the cohesion failure zone 83 may leave an imprint and/or residue of the test adhesive 42, generally a low texture region. Image processing may distinguish these failure regions, for example by pattern recognition and/or thresholding the image 80. For example, FIG. 12 illustrates a classification image 90 where each pixel of image 80 is classified as part of a laminal failure region 91, an interfacial failure region 92, or a cohesion failure region 93. The extent of failure of a particular type may be quantified by a parameter related to the image area of that failure in a classification image 90. The fraction of failure of a particular type may be quantified by a parameter related to the fractional image area of that failure in a classification image 90. Strong bonds may be classified as test bonds 40 where the predominant failure modes are at the laminal failure zone 81 and/or the cohesion failure zone 83. Additionally or alternatively, strong bonds may be classified as test bonds 40 where the fraction of failure at the interfacial failure zone 82 is less than 20%, less than 10%, less than 5%, less than 2%, and/or less than 1%. Weak bonds may be classified as test bonds 40 where the predominant failure mode is at the interfacial failure zone 82, optionally when the fraction of failure at the interfacial failure zone 82 is greater than 5%, greater than 10%, greater than 20%, and/or greater than 50%.

Further aspects of inventive subject matter are illustrated without limitation in the following illustrative, non-exclusive examples. These examples are included for illustration and are not intended to limit or define the entire scope of the present teachings.

Example 1

Rapid Adhesion Testing

Figure 13:
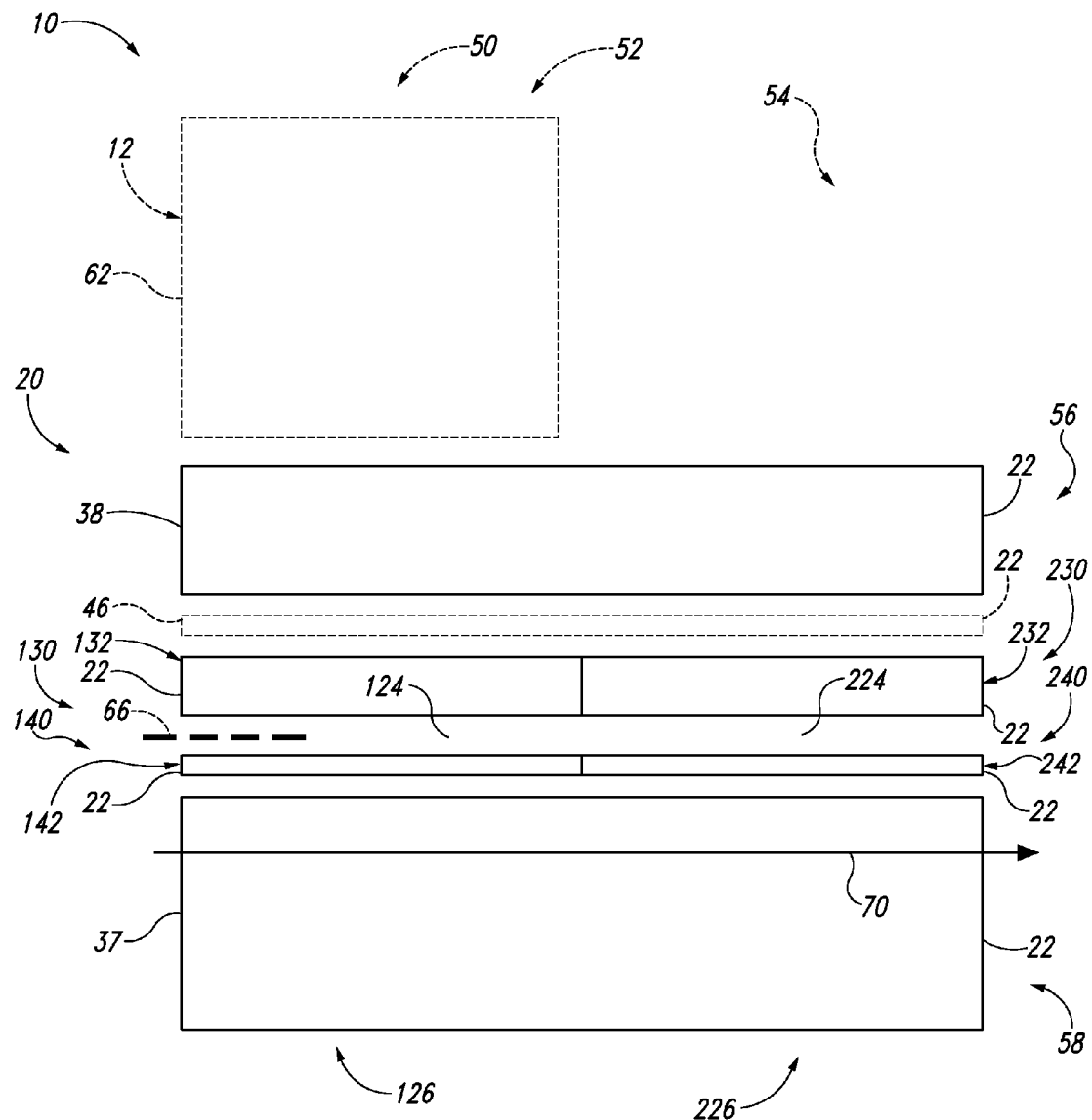
FIG. 13 is a schematic representation of test systems for rapid adhesion testing.

FIG. 13 is a schematic representation, in exploded view, of test systems 10 and test coupons 20 for rapid adhesion testing.

Rapid adhesion testing may be useful to simply and quickly interrogate a series of test bonds 40. The test coupons 20 comprise at least two test structures 30, namely a first test structure 130 and a second test structure 230. The first test structure 130 includes a first test adhesive 142 (a test adhesive 42), a first test adherend 132 (a test adherend 32), a first test interface 124 (a test interface 24 which is the interface between the first test adherend 132 and the first test adhesive 142), and a first test bond 140 (a test bond 40) to a first location 126 (a test region 26) on a base support 37. The second test structure 230 includes a second test adhesive 242 (a test adhesive 42), a second test adherend 232 (a test adherend 32), a second test interface 224 (a test interface 24 which is the interface between the second test adherend 232 and the second test adhesive 242), and a second test bond 240 (a test bond 40) to a second location 226 (a test region 26) on the base support 37.

The test coupons 20 comprise layers in the following sequence: (a) the base support 37, (b) an adhesive layer 22, including the first test adhesive 142 adjacent to the first location 126 and the second test adhesive 242 adjacent to the second location 226, (c) an adherend layer 22, including the first test adherend 132 adjacent to the first test adhesive 142 and the second test adherend 232 adjacent to the second test adhesive 242, and (d) a peeling support 38 bonded to the first test adherend 132 and bonded to the second test adherend 232. Further, the first test adherend 132 is coupled to the first location 126 on the base support 37 with the first test bond 140, including the first test adhesive 142, and the second test adherend 232 is coupled to the second location 226 on the base support 37 with the second test bond 240 including the second test adhesive 242. Test coupons 20 comprise a peeling structure 56, which includes the adherend layer 22 (layer c) and the peeling support 38 (layer d), and a backing structure 58, which includes the base support 37 (layer a). Peeling structures 56 are relatively thin, with a thickness generally less than 2 mm, less than 1.5 mm, less than 1 mm, less than 0.8 mm, and/or less than 0.5 mm. Backing structures 58 are relatively thick to provide rigidity, with a thickness generally greater than 0.8 mm, greater than 1 mm, greater than 1.5 mm, greater than 2 mm, and/or greater than 2.5 mm.

As the first test structure 130 and the second test structure 230 are sandwiched between the base support 37 and the peeling support 38, generally the thickness of the first test structure 130 and the second test structure 230 are approximately the same. For example, the first test adherend 132 and the second test adherend 232 may be essentially the same thickness, e.g., including the same number of plies.

The first test structure 130 and the second test structure 230 may share common components. For example, the first test adherend 132 and the second test adherend 232 may be the same test adherend 32. As another example, the first test adhesive 142 and the second test adhesive 242 may be the same test adhesive 42.

Test coupons 20 may comprise a crack starter 60 in the first test structure 130, at the edge of the first test interface 124 between the first test adherend 132 and the first test adhesive 142. Test coupons 20 may comprise a crack starter 60 in the second test structure 230, at the edge of the second test interface 224 between the second test adherend 232 and the second test adhesive 242. Each test structure 30 independently may include a crack starter 60. Additionally or alternatively, the test coupon 20 may comprise a single crack starter 60.

The first test adherend 132 and the second test adherend 232 each independently may be directly or indirectly bonded to the peeling support 38 (e.g., by curing the first test adherend 132 and/or the second test adherend 232 to the peeling support 38, and/or by using one or more structural adhesives 46).

The test coupon 20 is configured to peel apart along the peeling direction 70. The test coupon 20 may be configured with test structures 30 spaced along the peeling direction 70, as illustrated, and/or may be configured with test structures 30 spaced perpendicular to the peeling direction. When the test structures 30 are spaced along the peeling direction 70, the test coupon is configured to peel the test structures 30 sequentially.

Test systems 10 may include a test fixture 12 which may include a drum 62. The test fixture 12 is configured to pull the test coupon 20 apart between the backing structure 58 and the peeling structure 56 (generally at the first test bond 140 and the second test bond 240). The test fixture 12 is configured to apply a peeling force 50 at an angle to the test support 30, generally substantially perpendicular to the test support 30 layer 22, at least not essentially parallel to the layers 22 of the test coupon 20. The force application region 52 of the peeling structure 56 is coupled to the drum 62. For example, the drum 62 may define a slot configured to accept the force application region 52 of the peeling structure 56. Additionally or alternatively, the peeling structure 56 may be clamped to drum 62. The test fixture 12 is configured such that rolling the drum 62 rolls the peeling structure 56 around the drum 62 and peels the test coupon 20 at the test structures 30. Further, the test fixture 12 is configured to control the peeling angle by maintaining a substantially constant peeling angle. The peeling angle, and the required flexibility of the peeling structure 56, substantially is determined by the diameter of the drum 62. The drum 62 may have a diameter of at least 50 mm, at least 100 mm, at least 150 mm, and/or at least 200 mm.

Example 2

Backing Rapid Adhesion Testing

Figure 14:
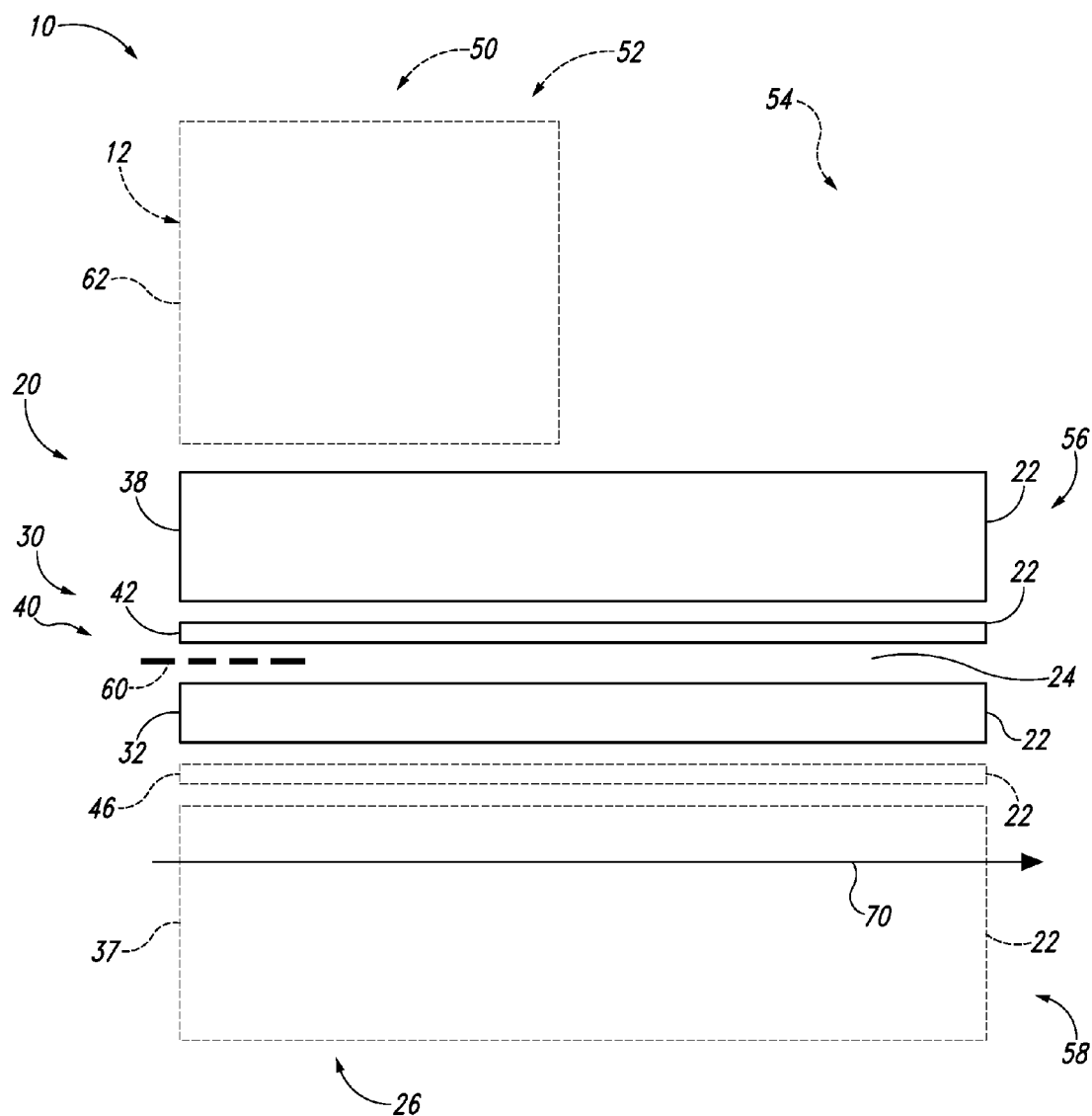
FIG. 14 is a schematic representation of test systems for backing rapid adhesion testing.

FIG. 14 is a schematic representation, in exploded view, of test systems 10 and test coupons 20 for backing rapid adhesion testing. Backing rapid adhesion testing may be suitable to interrogate a test bond 40 to a test adherend 32 that is rigid, e.g., too rigid to peel with the peeling support 38 in example 1, though test adherends 32 are not required to be rigid. Illustrative, non-exclusive examples of test adherends 32 suitable for backing rapid adhesion testing include frames, stringers, girders, and larger bonded assemblies. The test systems 10 and the test coupons 20 of this example 2 are configured to interrogate the test bond 40 coupled to the backing structure 58 rather than coupled to the peeling structure 56 (as is the case for example 1).

The test coupons 20 comprise a test structure 30 which includes a test adhesive 42, a test adherend 32, a test interface 24, and a test bond 40 to a peeling support 38. The test coupons 20 comprise layers in the following sequence: (a) the peeling support 38, (b) the test adhesive 42, (c) the test adherend 32, and optionally (d) a base support 37 bonded to the test adherend 32. Further, the test adherend 32 is coupled to the peeling support 38 with the test bond 40, including the test adhesive 42. The test adherend 32, the base support 37, and/or the combination of the two may be rigid. Test coupons 20 comprise the peeling structure 56, which includes the peeling support 38 (layer a), and the backing structure 58, which includes the test adherend 32 (layer c) and the optional base support 37 (layer d). The test adherend 32 may be directly or indirectly bonded to the base support 37 (e.g., by curing the test adherend 32 to the base support 37 and/or by using a structural adhesive 46). Relative properties, including thicknesses, of the peeling structures 56 and backing structures 58 are the same as example 1. Test coupons 20 may comprise a crack starter 60 in the test structure 30, at the edge of the test interface 24, between the test adherend 32 and the test adhesive 42.

Test systems 10 may include a test fixture 12 which may include a drum 62. Generally, the test fixtures 12 described with respect to example 1 are suitable for backing rapid adhesion testing as well.

Example 3

Double Cantilever Beam Testing

Figure 15:
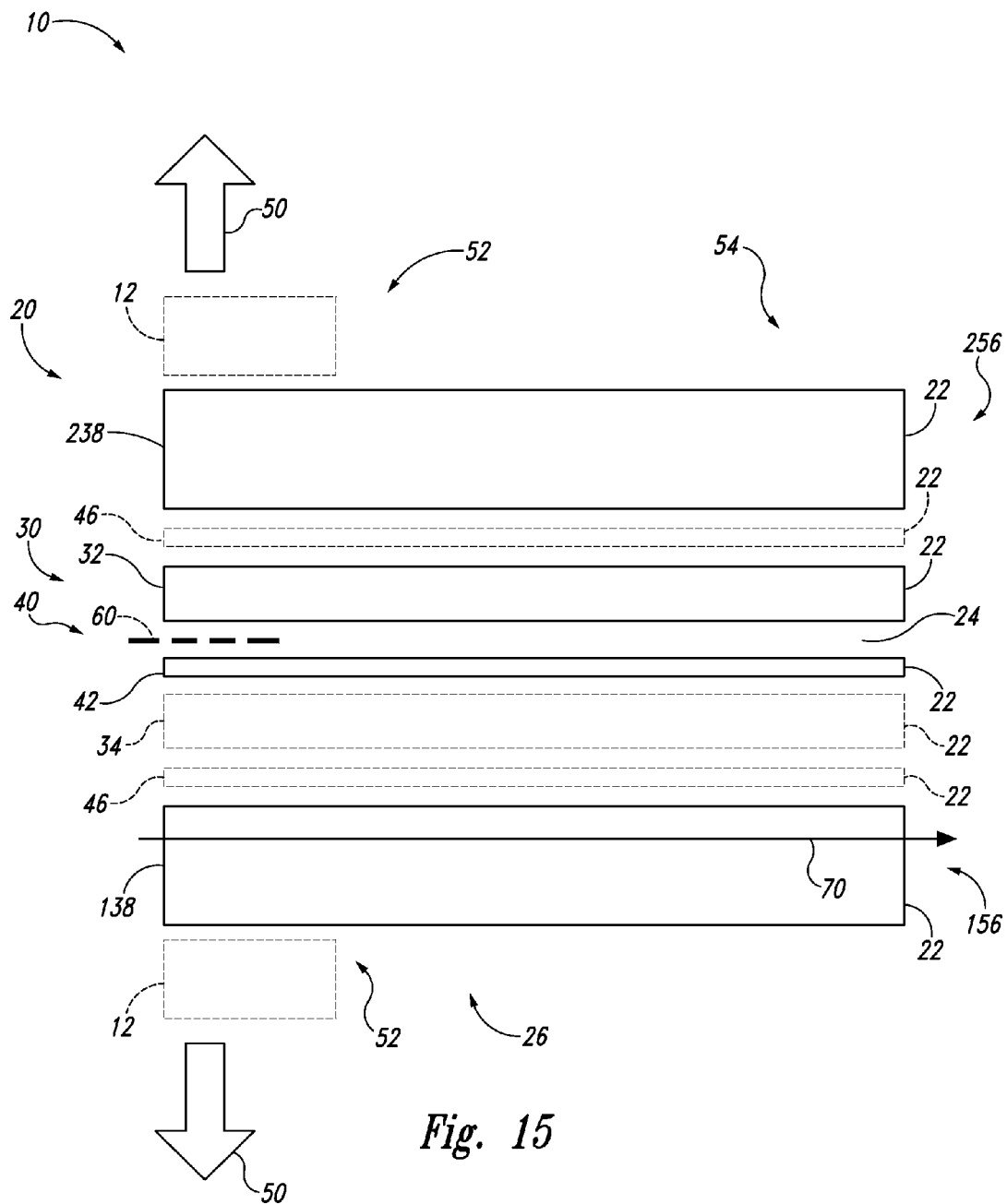
FIG. 15 is a schematic representation of test systems for modified double cantilever beam testing.

FIG. 15 is a schematic representation, in exploded view, of test systems 10 and test coupons 20 for double cantilever beam testing of test structures 30 including test adherends 32. This configuration may be suitable to interrogate a test bond 40 within a test structure 30 that includes a test adherend 32 (that is non-metallic) and a first peeling support 138 (a peeling support 38).

The test coupons 20 comprise a test structure 30 which includes a test adhesive 42, the test adherend 32, a test interface 24, and the test bond 40 to the first peeling support 138. The test coupons 20 comprise layers in the following sequence: (a) the first peeling support 138, (b) the test adhesive 42, (c) the test adherend 32, and (d) a second peeling support 238 (a peeling support 38) bonded to the test adherend 32. Further, the test adherend 32 is coupled to the first peeling support 138 with the test bond 40, including the test adhesive 42. Test coupons 20 comprise a first peeling structure 156, which includes the first peeling support 38 (layer a), and a second peeling structure 256, which includes the test adherend 32 (layer c) and the second peeling support 238 (layer d). The test adherend 32 may be directly or indirectly bonded to the second peeling support 238 (e.g., by curing the test adherend 32 to the second peeling support 238 and/or by using a structural adhesive 46). First peeling structure 156 and second peeling structure 256 each independently are relatively thin, with a thickness generally less than 2 mm, less than 1.5 mm, less than 1 mm, less than 0.8 mm, and/or less than 0.5 mm.

Test coupons 20 may comprise a peeling adherend 34 between the first peeling support 138 and the test adhesive 42. The peeling adherend 34 may be directly or indirectly bonded to the first peeling support 138 (e.g., by curing the peeling adherend 34 to the first peeling support 138 and/or by using a structural adhesive 46). The peeling adherend 34, when present, may be substantially the same as the test adherend 32. Test coupons 20 may comprise a crack starter 60 in the test structure 30, at the edge of the test interface 24, between the test adherend 32 and the test adhesive 42.

Example 4

Double Cantilever Beam Testing

Figure 16:
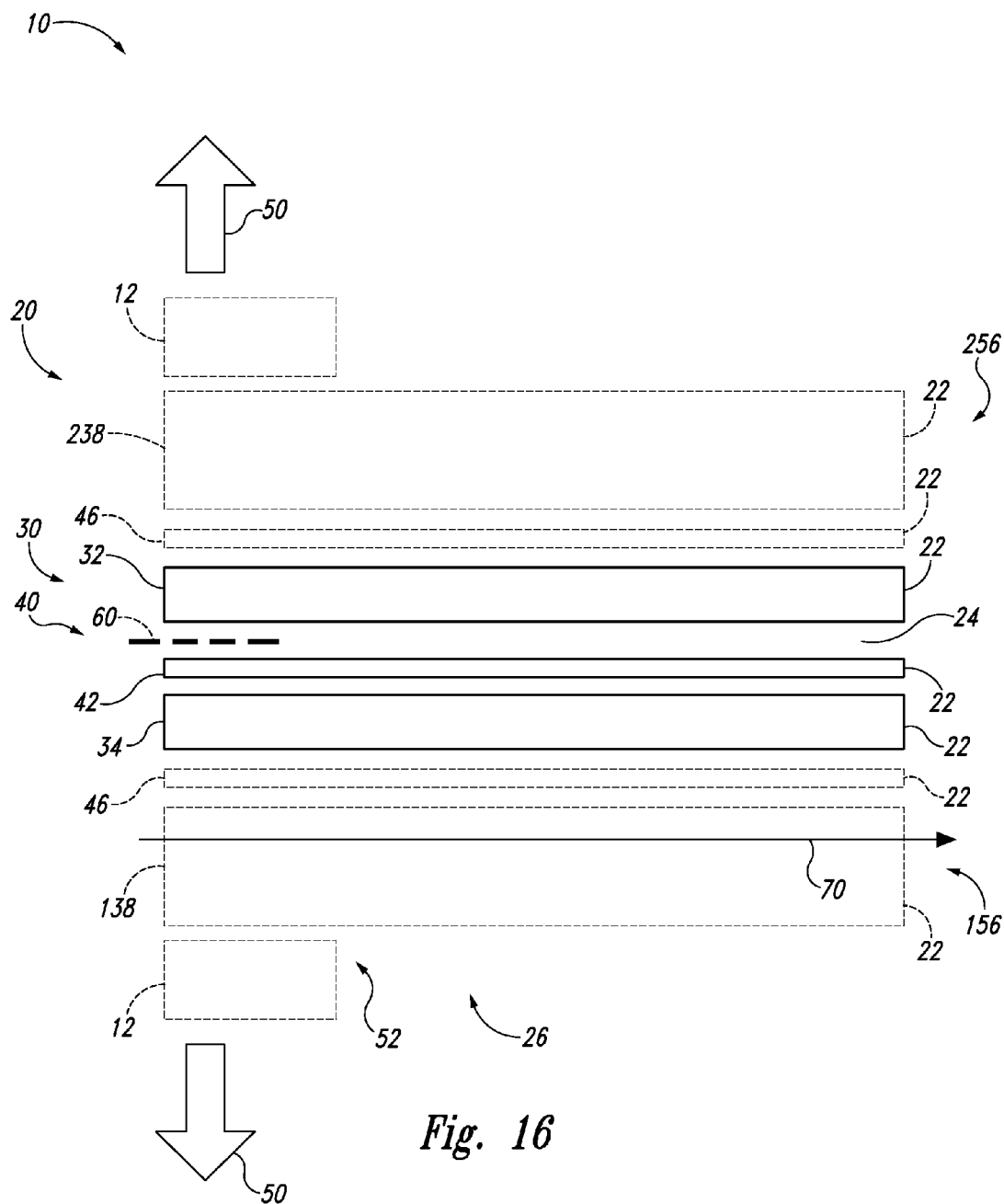
FIG. 16 is a schematic representation of test systems for back-bonded double cantilever beam testing.

FIG. 16 is a schematic representation, in exploded view, of test systems 10 and test coupons 20 for double cantilever beam testing of thin test structures 30. This configuration may be suitable to rapidly apply environmental conditions to the test structure 30 before bonding supports required for peel testing. For example, a thin test structure 30 may be wetted, aged, and/or heated faster than a thicker test structure 30.

The test coupons 20 comprise a test structure 30 which includes a test adhesive 42, a test adherend 32, a test interface 24, and a test bond 40 to a peeling adherend 34. The test coupons 20 comprise layers in the following sequence: (a) a first peeling support 138 (a peeling support 38) bonded to the peeling adherend 34, (b) the peeling adherend 34, (c) the test adhesive 42, (d) the test adherend 32, and (e) a second peeling support 238 (a peeling support 38) bonded to the test adherend 32. Further, the test adherend 32 is coupled to the peeling adherend 34 with the test bond 40, including the test adhesive 42. Test coupons 20 comprise a first peeling structure 156, which includes the first peeling support 138 (layer a) and the peeling adherend 34 (layer b), and a second peeling structure 256, which includes the test adherend 32 (layer d) and the second peeling support 238 (layer e). The peeling adherend 34 may be directly or indirectly bonded to the first peeling support 138 (e.g., by curing the peeling adherend 34 to the first peeling support 138 and/or by using a structural adhesive 46). The test adherend 32 may be directly or indirectly bonded to the second peeling support 238 (e.g., by curing the test adherend 32 to the second peeling support 238 and/or by using a structural adhesive 46). The peeling adherend 34 may be substantially the same as the test adherend 32. Hence, the test structure 30 may be a substantially symmetric structure.

The test adherend 32 and the peeling adherend 34 each independently may include one or more plies, for example less than 20 plies, less than 10 plies, less than 8 plies, less than 6 plies, less than 4 plies, about 20 plies, about 10 plies, 8 plies, 6 plies, 4 plies, 3 plies, 2 plies, 1 ply, 1-20 plies, 1-8 plies, and/or 1-4 plies. The first peeling support 138 may be a laminar material and may include more plies than the peeling adherend 34, for example, 1.5-8 times as many plies as the peeling adherend 34. The second peeling support 238 may be a laminar material and may include more plies than the test adherend 32, for example, 1.5-8 times as many plies as the test adherend 32. The total thickness of the peeling adherend 34 and the first peeling support 138 may be equivalent to at least 6 plies, at least 8 plies, at least 10 plies, and/or about 20 plies. The total thickness of the test adherend 32 and the second peeling support 238 may be equivalent to at least 6 plies, at least 8 plies, at least 10 plies, and/or about 20 plies.

The test structure 30 may be subject to environmental conditions before bonding to the first peeling support 138 and the second peeling support 238. After environmental conditions are applied the first peeling support 138 and the second peeling support 238 may be bonded to the test structure 30 such that the environmental conditioning is not substantially disturbed. For example, where temperature and/or moisture is a part of environmental conditioning, the first peeling support 138 and the second peeling support 238 may be bonded with room temperature cure structural adhesives 46.

Example 5

Double Cantilever Beam Testing

Figure 17:
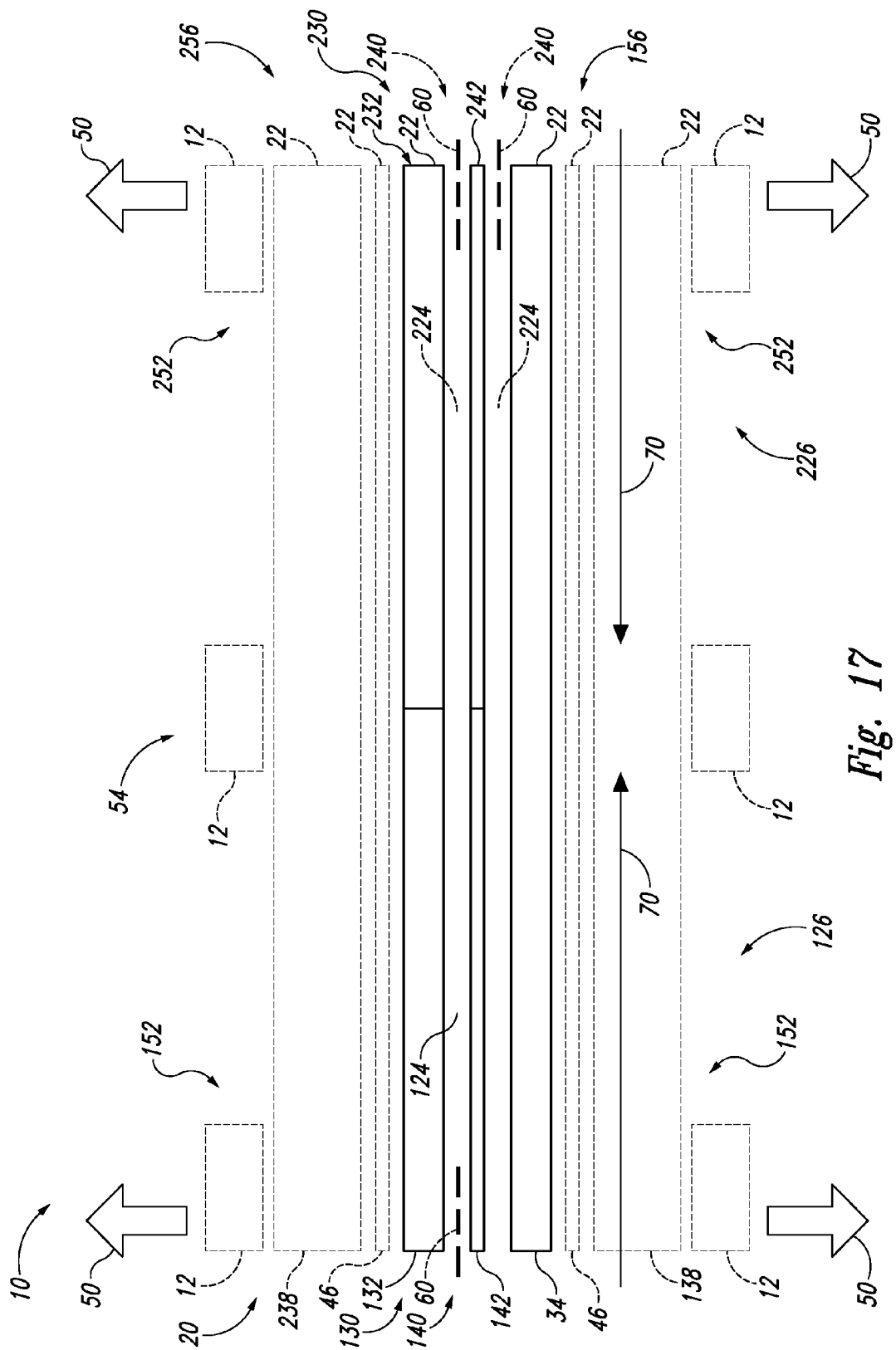
FIG. 17 is an illustrative, non-exclusive example of a pair of test structures in a test coupon.

FIG. 17 is a schematic representation, in exploded view, of test systems 10 and test coupons 20 for double cantilever beam testing of at least two test structures 30 within a test coupon 20. This configuration may be suitable for rapidly testing a series of test bonds 40 and/or to compare adhesive bonding schemes. Test structures 30, such as a first test structure 130 and a second test structure 230, may share components, as discussed with respect to example 1, and/or may be subject to the same environmental conditions. Hence, the first test structure 130 and the second test structure 230 may be analogous structures that essentially differ only in the adhesive bond scheme (if at all). Related samples may be used to reduce the effects of systematic and sample related errors that may be present in testing. For example, effects of batch to batch variation in preparation of test adherends 32 may be greatly reduced by comparing the results of testing a first test structure 130 and a second test structure 230 that share a test adherend 32.

Test coupons 20 comprise at least two test structures 30, namely a first test structure 130 and a second test structure 230. The first test structure 130 includes a first test adhesive 142 (a test adhesive 42), a first test adherend 132 (a test adherend 32), a first test interface 124 (a test interface 42 which is the interface between the first test adherend 132 and the first test adhesive 142), and a first test bond 140 (a test bond 40) to a first location 126 (a test region 26) on a peeling adherend 34. The second test structure 230 includes a second test adhesive 242 (a test adhesive 42), a second test adherend 232 (a test adherend 32), a second test interface 224 (a test interface 24 which is the interface between the second test adherend 232 and the second test adhesive 242), and a second test bond 240 (a test bond 40) to a second location 226 (a test region 26) on the peeling adherend 34.

The test coupons 20 comprise layers in the following sequence: (a) a first peeling support 138 (a peeling support 38) bonded to the peeling adherend 34, (b) the peeling adherend 34, (c) an adhesive layer 22, including the first test adhesive 142 adjacent to the first location 126 and the second test adhesive 242 adjacent to the second location 226, (d) an adherend layer 22, including the first test adherend 132 adjacent to the first test adhesive 142 and the second test adherend 232 adjacent to the second test adhesive 242, and (e) a second peeling support 238 (a peeling support 38) bonded to the first test adherend 132 and bonded to the second test adherend 232.

Further, the first test adherend 132 is coupled to the first location 126 on the peeling adherend 34 with the first test bond 140, including the first test adhesive 142, and the second test adherend 232 is coupled to the second location 226 on the peeling adherend 34 with the second test bond 240 including the second test adhesive 242. Test coupons 20 comprise a first peeling structure 156, which includes the first peeling support 138 (layer a) and the peeling adherend 34 (layer b), and a second peeling structure 256, which includes the adherend layer 22 (layer d) and the second peeling support 238 (layer e). The peeling adherend 34 may be directly or indirectly bonded to the first peeling support 138 (e.g., by curing the peeling adherend 34 to the first peeling support 138 and/or by using a structural adhesive 46). The first test adherend 132 may be directly or indirectly bonded to the second peeling support 238 (e.g., by curing the first test adherend 132 to the second peeling support 238 and/or by using a structural adhesive 46). The second test adherend 232 may be directly or indirectly bonded to the second peeling support 238 (e.g., by curing the second test adherend 232 to the second peeling support 238 and/or by using a structural adhesive 46). The peeling adherend 34 may be substantially the same as the first test adherend 132 and/or the second test adherend 232. Hence, the test structure 30 may be a substantially symmetric structure.

Test systems 10 may include a test fixture 12 configured to apply peeling forces 50 at the first force application region 152 of the first peeling structure 156 and at the first force application region 152 of the second peeling structure 256. The test fixture 12 may be configured to apply peeling forces 50 at the second force application region 252 of the first peeling structure 156 and at the second force application region 252 of the second peeling structure 256. Additionally or alternatively, the test fixture 12 may be configured to allow the test coupon 20 to be rotated such that the first force application region 152 and the second force application region 252 are swapped with respect to the test fixture 12.

Example 6

Wide Area Lap Shear Testing

Figure 18:
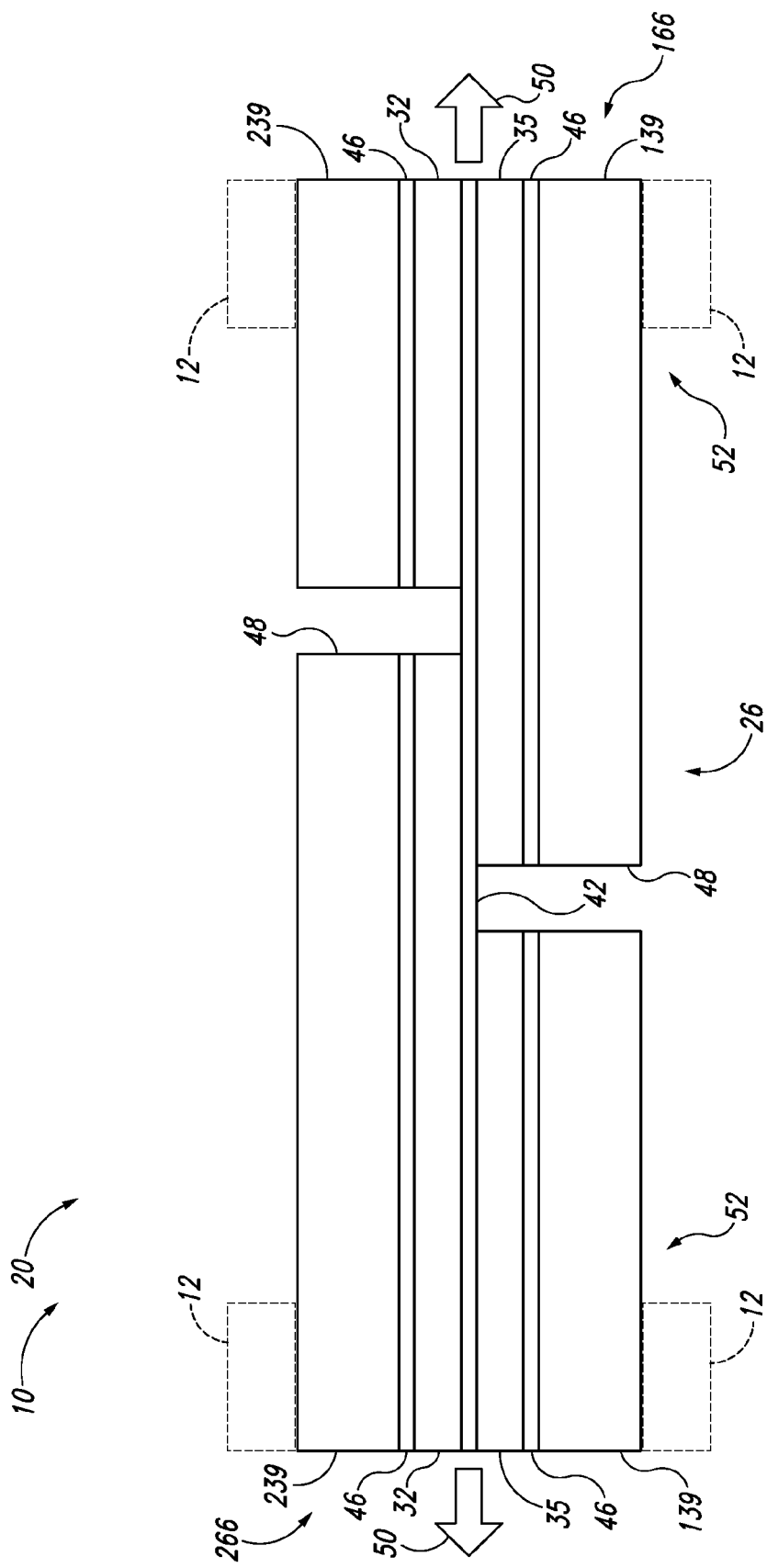
FIG. 18 is a schematic representation of test systems for modified wide area lap shear testing.

FIG. 18 is a schematic representation of test systems 10 and test coupons 20 for wide area lap shear testing of test structures including test adherends 32. This configuration may be suitable to interrogate a test bond 40 within a test structure 30 that includes a test adherend 32 (that is non-metallic) and a shearing adherend 35. Also, this configuration may be suitable to rapidly apply environmental conditions to the test structure 30 before bonding supports required for shear testing. For example, a thin test structure 30 may be wetted, aged, and/or heated faster than a thicker test structure 30.

The test coupons 20 comprise a test structure 30 which includes a test adhesive 42, a test adherend 32, a test interface 24, and a test bond 40 to a shearing adherend 35. The test coupons 20 comprise layers in the following sequence: (a) a first shearing support 139 (a shearing support 39) bonded to the shearing adherend 35, (b) the shearing adherend 35, (c) the test adhesive 42, (d) the test adherend 32, and (e) a second shearing support 239 (a shearing support 39) bonded to the test adherend 32. Further, the test adherend 32 is coupled to the shearing adherend 35 with the test bond 40, including the test adhesive 42. Test coupons 20 comprise a first shearing structure 166 (a shearing structure 66), which includes the first shearing support 139 (layer a) and the shearing adherend 35 (layer b), and a second shearing structure 266 (a shearing structure 66), which includes the test adherend 32 (layer d) and the second shearing support 239 (layer e). The shearing adherend 35 may be directly or indirectly bonded to the first shearing support 139 (e.g., by curing the shearing adherend 35 to the first shearing support 139 and/or by using a structural adhesive 46). The test adherend 32 may be directly or indirectly bonded to the second shearing support 239 (e.g., by curing the test adherend 32 to the second shearing support 239 and/or by using a structural adhesive 46). The shearing adherend 35 may be substantially the same as the test adherend 32. Hence, the test structure 30 may be a substantially symmetric structure.

The test adherend 32 and the shearing adherend 35 each independently may include one or more plies, for example less than 20 plies, less than 10 plies, less than 8 plies, less than 6 plies, less than 4 plies, about 20 plies, about 10 plies, 8 plies, 6 plies, 4 plies, 3 plies, 2 plies, 1 ply, 1-20 plies, 1-8 plies, and/or 1-4 plies. The first shearing support 139 may be a laminar material and may include more plies than the shearing adherend 35, for example, 1.5-8 times as many plies as the shearing adherend 35. The second shearing support 239 may be a laminar material and may include more plies than the test adherend 32, for example, 1.5-8 times as many plies as the test adherend 32. The total thickness of the shearing adherend 35 and the first shearing support 139 may be equivalent to at least 6 plies, at least 8 plies, at least 10 plies, and/or about 20 plies. The total thickness of the test adherend 32 and the second shearing support 239 may be equivalent to at least 6 plies, at least 8 plies, at least 10 plies, and/or about 20 plies.

The test structure 30 may be subject to environmental conditions before bonding to the first shearing support 139 and the second shearing support 239. After environmental conditions are applied the first shearing support 139 and the second shearing support 239 may be bonded to the test structure 30 such that the environmental conditioning is not substantially disturbed. For example, where temperature and/or moisture is a part of environmental conditioning, the first shearing support 139 and the second shearing support 239 may be bonded with room temperature cure structural adhesives 46.

Illustrative, non-exclusive examples of inventive subject matter according to the present disclosure are described in the following enumerated paragraphs:

A1. A method of fabricating a layered test coupon, the method comprising:

adhering a first test adherend with a first test adhesive to a first location on a base support to create a first test bond, wherein the first test adherend is non-metallic;

adhering a second test adherend with a second test adhesive to a second location on the base support to create a second test bond, wherein the second location is adjacent the first location, and wherein the second test adherend is non-metallic;

bonding the first test adherend to a peeling support; and bonding the second test adherend to the peeling support.

A2. The method of paragraph A1, wherein the adhering the first test adherend includes applying the first test adhesive between the first test adherend and the first location of the base support.

A3. The method of any of paragraphs A1-A2, wherein the adhering the second test adherend includes applying the second test adhesive between the second test adherend and the second location of the base support.

A4. The method of any of paragraphs A1-A3, wherein the adhering the first test adherend includes curing the first test adhesive, optionally at a temperature above 20° C., above 70° C., above 100° C., above 150° C., about 20° C., about 70° C., about 120° C., about 180° C., 20° C.-200° C., 20° C.-100° C., 100° C.-200° C., and/or 150° C.-200° C.

A5. The method of any of paragraphs A1-A4, wherein the adhering the second test adherend includes curing the second test adhesive, optionally at a temperature above 20° C., above 70° C., above 100° C., above 150° C., about 20° C., about 70° C., about 120° C., about 180° C., 20° C.-200° C., 20° C.-100° C., 100° C.-200° C., and/or 150° C.-200° C.

A6. The method of any of paragraphs A1-A5, wherein the adhering the first test adherend and the adhering the second test adherend include curing the first test adhesive and curing the second test adhesive under the same conditions.

A7. The method of any of paragraphs A1-A6, wherein the adhering the first test adherend and the adhering the second test adherend are performed at least partially concurrently.

A8. The method of any of paragraphs A1-A7, wherein the adhering the first test adherend includes curing the first test adherend and the first test adhesive at least partially concurrently.

A9. The method of any of paragraphs A1-A8, wherein the adhering the second test adherend includes curing the second test adherend and the second test adhesive at least partially concurrently.

A10. The method of any of paragraphs A1-A9, wherein the bonding the first test adherend includes curing the first test adherend onto the peeling support.

A11. The method of any of paragraphs A1-A10, wherein the bonding the second test adherend includes curing the second test adherend onto the peeling support.

A12. The method of any of paragraphs A1-A11, wherein the bonding the first test adherend and the adhering the first test adherend are performed at least partially concurrently.

A13. The method of any of paragraphs A1-A12, wherein the bonding the second test adherend and the adhering the second test adherend are performed at least partially concurrently.

A14. The method of any of paragraphs A1-A13, wherein the bonding the first test adherend and the bonding the second test adherend are performed at least partially concurrently.

A15. The method of any of paragraphs A1-A14, wherein the bonding the first test adherend includes applying a structural adhesive between the first test adherend and the peeling support, and optionally includes curing the structural adhesive.

A16. The method of any of paragraphs A1-A15, wherein the bonding the second test adherend includes applying a structural adhesive between the second test adherend and the peeling support, and optionally includes curing the structural adhesive.

A17. The method of any of paragraphs A1-A16, further comprising:

placing a first crack starter between the first test adhesive and the first test adherend before the adhering the first test adherend, optionally wherein the first crack starter includes at least one of FEP, PTFE, and silicone.

A18. The method of any of paragraphs A1-A17, further comprising:

placing a second crack starter between the second test adhesive and the second test adherend before the adhering the second test adherend, optionally wherein the second crack starter includes at least one of FEP, PTFE, and silicone.

A19. The method of any of paragraphs A1-A18, wherein the first test adherend includes less than 20 plies, less than 10 plies, less than 8 plies, less than 6 plies, less than 4 plies, about 20 plies, about 10 plies, 8 plies, 6 plies, 4 plies, 3 plies, 2 plies, 1 ply, 1-20 plies, 1-8 plies, and/or 1-4 plies.

A20. The method of any of paragraphs A1-A19, wherein the second test adherend includes less than 20 plies, less than 10 plies, less than 8 plies, less than 6 plies, less than 4 plies, about 20 plies, about 10 plies, 8 plies, 6 plies, 4 plies, 3 plies, 2 plies, 1 ply, 1-20 plies, 1-8 plies, and/or 1-4 plies.

A21. The method of any of paragraphs A1-A20, wherein the peeling support consists essentially of at least one of metal, aluminum alloy, and steel.

A22. The method of any of paragraphs A1-A21, wherein the base support includes at least one of metal, aluminum alloy, steel, polymeric material, plastic, laminar material, composite material, fiber-reinforced plastic, mineral-filled plastic, glass, and ceramic.

A23. The method of any of paragraphs A1-A22, further comprising:

fabricating the first test adherend.

A24. The method of any of paragraphs A1-A23, further comprising:

fabricating the second test adherend.

A25. The method of any of paragraphs A1-A24, further comprising:

curing the first test adherend.

A26. The method of any of paragraphs A1-A25, further comprising:

curing the second test adherend.

A27. The method of any of paragraphs A1-A26, further comprising:

preparing a surface of the first test adherend for adhering to the first location on the base support.

A27.1. The method of paragraph A27, wherein the preparing includes peeling a peel ply from the first test adherend.

A28. The method of any of paragraphs A1-A27.1, further comprising:

preparing a surface of the second test adherend for adhering to the second location on the base support.

A28.1. The method of paragraph A28, wherein the preparing includes peeling a peel ply from the first test adherend.

A29. The method of any of paragraphs A1-A28.1, wherein the first test adherend is laminar and/or composite, and optionally wherein the first test adherend includes at least one of a laminar material, a composite material, a fiber-reinforced plastic, a mineral-filled plastic, a polymeric material, a plastic, a glass, and a ceramic material.

A30. The method of any of paragraphs A1-A29, wherein the second test adherend is laminar and/or composite, and optionally wherein the second test adherend includes at least one of a laminar material, a composite material, a fiber-reinforced plastic, a mineral-filled plastic, a polymeric material, a plastic, a glass, and a ceramic material.

A31. A layered test coupon fabricated according to any of the methods of paragraphs A1-A30.

A32. A layered test coupon comprising layers in the following sequence:
a base support with a first location and a second location,
an adhesive layer including a first test adhesive adjacent to the first location and a second test adhesive adjacent to the second location,
an adherend layer including a first test adherend that is non-metallic and a second test adherend that is non-metallic, and
a peeling support bonded to the first test adherend and bonded to the second test adherend;
wherein the first test adherend is coupled to the first location on the base support with a first test bond including the first test adhesive, and wherein the second test adherend is coupled to the second location on the base support with a second test bond including the second test adhesive.

A32.1. The layered test coupon of paragraph A32, further comprising:
a first crack starter between the first test adhesive and the first test adherend, optionally wherein the first crack starter includes at least one of FEP, PTFE, and silicone.

A32.2. The layered test coupon of any of paragraphs A32-A32.1, further comprising:
a second crack starter between the second test adhesive and the second test adherend, optionally wherein the second crack starter includes at least one of FEP, PTFE, and silicone.

A32.3. The layered test coupon of any of paragraphs A32-A32.2, wherein the first test adherend includes less than 20 plies, less than 10 plies, less than 8 plies, less than 6 plies, less than 4 plies, about 20 plies, about 10 plies, 8 plies, 6 plies, 4 plies, 3 plies, 2 plies, 1 ply, 1-20 plies, 1-8 plies, and/or 1-4 plies.

A32.4. The layered test coupon of any of paragraphs A32-A32.3, wherein the second test adherend includes less than 20 plies, less than 10 plies, less than 8 plies, less than 6 plies, less than 4 plies, about 20 plies, about 10 plies, 8 plies, 6 plies, 4 plies, 3 plies, 2 plies, 1 ply, 1-20 plies, 1-8 plies, and/or 1-4 plies.

A32.5. The layered test coupon of any of paragraphs A32-A32.4, wherein the peeling support consists essentially of at least one of metal, aluminum alloy, and steel.

A32.6. The layered test coupon of any of paragraphs A32-A32.5, wherein the base support includes at least one of metal, aluminum alloy, steel, polymeric material, plastic, laminar material, composite material, fiber-reinforced plastic, glass, and ceramic.

A32.7. The layered test coupon of any of paragraphs A32-A32.6, wherein the first test adherend is laminar and/or composite, and optionally wherein the first test adherend includes at least one of a laminar material, a composite material, a fiber-reinforced plastic, a mineral-filled plastic, a polymeric material, a plastic, a glass, and a ceramic material.

A32.8. The layered test coupon of any of paragraphs A32-A32.7, wherein the first test adherend is laminar and/or composite, and optionally wherein the first test adherend includes at least one of a laminar material, a composite material, a fiber-reinforced plastic, a mineral-filled plastic, a polymeric material, a plastic, a glass, and a ceramic material.

A33. A method of testing a quality of bonds to non-metallic materials, the method comprising:
selecting the layered test coupon of any of paragraphs A31-A32.8; and
peeling the peeling support from the base support to test a strength of the first test bond and a strength of the second test bond.

A34. A method of testing a quality of bonds to non-metallic materials, the method comprising:
fabricating a layered test coupon according to the method of any of paragraphs A1-A30; and
peeling the peeling support from the base support to test a strength of the first test bond and a strength of the second test bond.

A35. The method of any of paragraphs A33-A34, further comprising:
initiating a crack in the first test bond by applying a wedge between the peeling support and the base support.

A36. The method of any of paragraphs A33-A35, further comprising:
initiating a crack in the second test bond by applying a wedge between the peeling support and the base support.

A37. The method of any of paragraphs A33-A36, wherein the peeling includes attaching a peeling mechanism to the peeling support and applying a force with the peeling mechanism to peel the peeling support from the base support.

A37.1. The method of paragraph A37, wherein the peeling mechanism is a drum, and wherein the peeling includes rolling at least a portion of the peeling support around the drum.

A38. The method of any of paragraphs A33-A37.1, wherein the peeling includes controlling the angle of the peeling support relative to the base support as the peeling support separates from the base support.

A39. The method of any of paragraphs A33-A38, further comprising:
classifying a failure mode of the first test bond, optionally wherein the classifying includes electronic imaging the first test bond after the peeling.

A40. The method of any of paragraphs A33-A39, further comprising:
classifying a failure mode of the second test bond, optionally wherein the classifying includes electronic imaging the second test bond after the peeling.

A41. The method of any of paragraphs A33-A40, further comprising:
quantifying an extent of failure of the first test bond.

A41.1. The method of paragraph A41, wherein the quantifying includes electronic imaging the first test bond after the peeling.

A41.2. The method of any of paragraphs A41-A41.1, wherein the quantifying includes determining at least one of a fraction of laminal failure, a fraction of interfacial failure, a fraction of cohesion failure, an extent of laminal failure, an extent of interfacial failure, and an extent of cohesion failure.

A42. The method of any of paragraphs A33-A41.2, further comprising:
quantifying an extent of failure of the second test bond.

A42.1. The method of paragraph A42, wherein the quantifying includes electronic imaging the second test bond after the peeling.

A42.2. The method of any of paragraphs A42-A42.1, wherein the quantifying includes determining at least one of a fraction of laminal failure, a fraction of interfacial failure, a fraction of cohesion failure, an extent of laminal failure, an extent of interfacial failure, and an extent of cohesion failure.

B1. A method of fabricating a layered test coupon, the method comprising:

adhering a test adherend with a test adhesive to a peeling support to create a test bond, wherein the test adherend is non-metallic, and wherein the test adherend is a base support that is rigid.

B2. A method of fabricating a layered test coupon, the method comprising:

adhering a test adherend with a test adhesive to a peeling support to create a test bond, wherein the test adherend is non-metallic; and bonding the test adherend to a base support that is rigid.

B2.1. The method of paragraph B2, wherein the bonding the test adherend includes curing the test adherend onto the base support.

B2.2. The method of any of paragraphs B2-B2.1, wherein the bonding the test adherend and the adhering the test adherend are performed at least partially concurrently.

B2.3. The method of any of paragraphs B2-B2.2, wherein the bonding the test adherend includes applying a structural adhesive between the test adherend and the base support, and optionally includes curing the structural adhesive.

B2.4. The method of any of paragraphs B2-B2.3, wherein the base support includes at least one of metal, aluminum alloy, steel, polymeric material, plastic, laminar material, composite material, fiber-reinforced plastic, mineral-filled plastic, glass, and ceramic.

B2.4.1. The method of paragraph B2.4, wherein the base support is laminar.

B2.4.2. The method of any of paragraphs B2.4-B2.4.1, wherein the base support is composite.

B2.4.3. The method of any of paragraphs B2.4-B2.4.2, wherein the base support consists essentially of fiber-reinforced plastic.

B3. The method of any of paragraphs B1-B2.4.3, wherein the adhering the test adherend includes applying the test adhesive between the test adherend and the peeling support.

B4. The method of any of paragraphs B1-B3, wherein the adhering the test adherend includes curing the test adhesive, optionally at a temperature above 20° C., above 70° C., above 100° C., above 150° C., about 20° C., about 70° C., about 120° C., about 180° C., 20° C.-200° C., 20° C.-100° C., 100° C.-200° C., and/or 150° C.-200° C.

B5. The method of any of paragraphs B1-B4, wherein the adhering the test adherend includes curing the test adherend and the test adhesive at least partially concurrently.

B6. The method of any of paragraphs B1-B5, further comprising:

placing a crack starter between the test adhesive and the test adherend before the adhering the test adherend, optionally wherein the crack starter includes at least one of FEP, PTFE, and silicone.

B7. The method of any of paragraphs B1-B6, wherein the test adherend includes less than 20 plies, less than 10 plies, less than 8 plies, less than 6 plies, less than 4 plies, about 20 plies, about 10 plies, 8 plies, 6 plies, 4 plies, 3 plies, 2 plies, 1 ply, 1-20 plies, 1-8 plies, 1-4 plies, 8-20 plies, 8-40 plies, greater than 8 plies, greater than 10 plies, and/or greater than 20 plies.

B8. The method of any of paragraphs B1-B7, wherein the peeling support consists essentially of at least one of metal, aluminum alloy, and steel.

B9. The method of any of paragraphs B1-B8, further comprising:

fabricating the test adherend.

B10. The method of any of paragraphs B1-B9, further comprising:

curing the test adherend.

B11. The method of any of paragraphs B1-B10, further comprising:

preparing a surface of the test adherend for adhering to the peeling support.

B11.1. The method of paragraph B11, wherein the preparing includes peeling a peel ply from the test adherend.

B12. The method of any of paragraphs B1-B11.1, wherein the test adherend is laminar and/or composite, and optionally wherein the test adherend includes at least one of a laminar material, a composite material, a fiber-reinforced plastic, a mineral-filled plastic, a polymeric material, a plastic, a glass, and a ceramic material.

B13. A layered test coupon fabricated according to any of the methods of paragraphs B1-B12.

B14. A layered test coupon comprising layers in the following sequence:

a peeling support, a test adhesive, and a test adherend that is non-metallic and that is a base support that is rigid;

wherein the test adherend is coupled to the peeling support with a test bond including the test adhesive.

B15. A layered test coupon comprising layers in the following sequence:

a peeling support, a test adhesive, a test adherend that is non-metallic, and a base support that is rigid;

wherein the test adherend is coupled to the peeling support with a test bond including the test adhesive, and wherein the base support is bonded to the test adherend.

B15.1. The layered test coupon of paragraph B15, wherein the base support includes at least one of metal, aluminum alloy, steel, polymeric material, plastic, laminar material, composite material, fiber-reinforced plastic, mineral-filled plastic, glass, and ceramic.

B15.1.1. The layered test coupon of paragraph B15.1, wherein the base support is laminar.

B15.1.2. The layered test coupon of any of paragraphs B15.1-B15.1.1, wherein the base support is composite.

B15.1.3. The layered test coupon of any of paragraphs B15.1-B15.1.2, wherein the base support consists essentially of fiber-reinforced plastic.

B15.2. The layered test coupon of any of paragraphs B15-B15.1.3, further comprising:

a structural adhesive between the base support and the test adherend, optionally wherein the structural adhesive is at least one of a room temperature adhesive, a pressure sensitive adhesive, and a contact adhesive.

B16. The layered test coupon of any of paragraphs B14-B15.2, further comprising:

a crack starter between the test adhesive and the test adherend, optionally wherein the crack starter includes at least one of FEP, PTFE, and silicone.

B17. The layered test coupon of any of paragraphs B14-B16, wherein the test adherend includes less than 20 plies, less than 10 plies, less than 8 plies, less than 6 plies, less than 4 plies, about 20 plies, about 10 plies, 8 plies, 6 plies, 4 plies, 3 plies, 2 plies, 1 ply, 1-20 plies, 1-8 plies, 1-4 plies, 8-20 plies, 8-40 plies, greater than 8 plies, greater than 10 plies, and/or greater than 20 plies.

B18. The layered test coupon of any of paragraphs B14-B17, wherein the peeling support consists essentially of at least one of metal, aluminum alloy, and steel.

B19. The layered test coupon of any of paragraphs B14-B18, wherein the test adherend is laminar and/or composite, and optionally wherein the test adherend includes at least one of a laminar material, a composite material, a fiber-reinforced plastic, a mineral-filled plastic, a polymeric material, a plastic, a glass, and a ceramic material.

B20. A method of testing a quality of a bond to non-metallic materials, the method comprising:
selecting the layered test coupon of any of paragraphs B13-B19; and
peeling the peeling support from the base support to test a strength of the test bond.

B21. A method of testing a quality of a bond to non-metallic materials, the method comprising:
fabricating a layered test coupon according to the method of any of paragraphs B1-B12; and
peeling the peeling support from the base support to test a strength of the test bond.

B22. The method of any of paragraphs B20-B21, further comprising:
initiating a crack in the test bond by applying a wedge between the peeling support and the base support.

B23. The method of any of paragraphs B20-B22, wherein the peeling includes attaching a peeling mechanism to the peeling support and applying a force with the peeling mechanism to peel the peeling support from the base support.

B23.1. The method of paragraph B23, wherein the peeling mechanism is a drum, and wherein the peeling includes rolling at least a portion of the peeling support around the drum.

B24. The method of any of paragraphs B20-B23.1, wherein the peeling includes controlling the angle of the peeling support relative to the base support as the peeling support separates from the base support.

B25. The method of any of paragraphs B20-B24, further comprising:
classifying a failure mode of the test bond, optionally wherein the classifying includes electronic imaging the test bond after the peeling.

B26. The method of any of paragraphs B20-B25, further comprising:
quantifying an extent of failure of the test bond.

B26.1. The method of paragraph B26, wherein the quantifying includes electronic imaging the test bond after the peeling.

B26.2. The method of any of paragraphs B26-B26.1, wherein the quantifying includes determining at least one of a fraction of laminal failure, a fraction of interfacial failure, a fraction of cohesion failure, an extent of laminal failure, an extent of interfacial failure, and an extent of cohesion failure.

C1. A method of fabricating a layered test coupon, the method comprising:
adhering a test adherend with a test adhesive to a first peeling support to create a test bond and to form a test structure, wherein the test adherend is non-metallic; and
bonding the test adherend to a second peeling support.

C2. The method of paragraph C1, wherein the adhering the test adherend includes applying the test adhesive between the test adherend and the first peeling support.

C3. The method of any of paragraphs C1-C1.1, further comprising:
preparing a surface of the test adherend for adhering to the first peeling support.

C4. The method of paragraph C1.2, wherein the preparing includes peeling a peel ply from the test adherend.

C5. The method of any of paragraphs C1-C1.2.1, further comprising:
applying test conditions to the test structure prior to the bonding the test adherend, optionally wherein the applying includes at least one of wetting, aging, and heating.

C6. The method of paragraph C1.3, wherein the applying is performed for less than 100 days, less than 50 days, less than 20 days, less than 15 days, less than 10 days, less than 200 hours, less than 150 hours, less than 100 hours, at least 48 hours, at least 72 hours, at least 100 hours, at least 150 hours, at least 200 hours, at least 10 days, 48 hours—100 days, 48 hours—20 days, and/or 100 hours—20 days.

C7. The method of any of paragraphs C1-C1.3.1, wherein the test adhesive is a first test adhesive, wherein the test bond is a first test bond, wherein the adhering includes adhering the test adherend with the first test adhesive to a first location on the first peeling support to create the first test bond and includes adhering the test adherend with a second test adhesive to a second location on the first peeling support to create a second test bond.

C8. The method of any of paragraphs C1-C1.4, wherein the test adherend is a first test adherend, wherein the test bond is a first test bond, wherein the adhering includes adhering the first test adherend with the test adhesive to a first location on the first peeling support to create the first test bond and includes adhering a second test adherend with the test adhesive to a second location on the first peeling support to create a second test bond.

C9. A method of fabricating a layered test coupon, the method comprising:
adhering a test adherend with a test adhesive to a peeling adherend to create a test bond and to form a test structure, wherein the test adherend is non-metallic, and wherein the peeling adherend is non-metallic;
bonding the peeling adherend to a first peeling support; and
bonding the test adherend to a second peeling support.

C10. The method of paragraph C2, wherein the bonding the peeling adherend includes curing the peeling adherend onto the first peeling support.

C11. The method of any of paragraphs C2-C2.1, wherein the bonding the peeling adherend and the adhering the test adherend are performed at least partially concurrently.

C12. The method of any of paragraphs C2-C2.2, wherein the bonding the peeling adherend and the bonding the test adherend are performed at least partially concurrently.

C13. The method of any of paragraphs C2-C2.3, wherein the bonding the peeling adherend includes applying a structural adhesive between the peeling adherend and the first peeling support, and optionally includes curing the structural adhesive.

C14. The method of paragraph C2.4, wherein the structural adhesive is at least one of a room temperature adhesive, a pressure sensitive adhesive, and a contact adhesive.

C15. The method of any of paragraphs C2-C2.4.1, wherein the adhering the test adherend includes applying the test adhesive between the test adherend and the peeling adherend.

C16. The method of any of paragraphs C2-C2.5, wherein the adhering the test adherend includes curing the peeling adherend and the test adhesive at least partially concurrently.

C17. The method of any of paragraphs C2-C2.6, wherein the peeling adherend includes less than 20 plies, less than 10 plies, less than 8 plies, less than 6 plies, less than 4 plies, about 20 plies, about 10 plies, 8 plies, 6 plies, 4 plies, 3 plies, 2 plies, 1 ply, 1-20 plies, 1-8 plies, and/or 1-4 plies.

C18. The method of any of paragraphs C2-C2.7, further comprising:
fabricating the peeling adherend.

C19. The method of any of paragraphs C2-C2.8, further comprising:
curing the peeling adherend.

C20. The method of any of paragraphs C2-C2.9, further comprising:
preparing a surface of the test adherend for adhering to the peeling adherend.

C21. The method of paragraph C2.10, wherein the preparing includes peeling a peel ply from the test adherend.

C22. The method of any of paragraphs C2-C2.10.1, further comprising:
applying test conditions to the test structure prior to the bonding the peeling adherend and the bonding the test adherend, optionally wherein the applying includes at least one of wetting, aging, and heating.

C23. The method of paragraph C2.11, wherein the applying is performed for less than 100 days, less than 50 days, less than 20 days, less than 15 days, less than 10 days, less than 200 hours, less than 150 hours, less than 100 hours, at least 48 hours, at least 72 hours, at least 100 hours, at least 150 hours, at least 200 hours, at least 10 days, 48 hours—100 days, 48 hours—20 days, and/or 100 hours—20 days.

C24. The method of any of paragraphs C2-C2.11.1, wherein the test adhesive is a first test adhesive, wherein the test bond is a first test bond, wherein the adhering includes adhering the test adherend with the first test adhesive to a first location on the peeling adherend to create the first test bond and includes adhering the test adherend with a second test adhesive to a second location on the peeling adherend to create a second test bond.

C25. The method of any of paragraphs C2-C2.12, wherein the test adherend is a first test adherend, wherein the test bond is a first test bond, wherein the adhering includes adhering the first test adherend with the test adhesive to a first location on the peeling adherend to create the first test bond and includes adhering a second test adherend with the test adhesive to a second location on the peeling adherend to create a second test bond.

C26. The method of any of paragraphs C2-C2.13, wherein the peeling adherend is substantially the same as the test adherend.

C27. The method of any of paragraphs C2-C2.14, wherein the peeling adherend is laminar and/or composite, and optionally wherein the peeling adherend includes at least one of a laminar material, a composite material, a fiber-reinforced plastic, a mineral-filled plastic, a polymeric material, a plastic, a glass, and a ceramic material.

C28. The method of any of paragraphs C1-C2.15, wherein the bonding the test adherend includes curing the test adherend onto the second peeling support.

C29. The method of any of paragraphs C1-C3, wherein the bonding the test adherend and the adhering the test adherend are performed at least partially concurrently.

C30. The method of any of paragraphs C1-C4, wherein the bonding the test adherend includes applying a structural adhesive between the test adherend and the second peeling support, and optionally includes curing the structural adhesive.

C31. The method of paragraph C5, wherein the structural adhesive is at least one of a room temperature adhesive, a pressure sensitive adhesive, and a contact adhesive.

C32. The method of any of paragraphs C1-05.1, wherein the adhering the test adherend includes curing the test adhesive, optionally at a temperature above 20° C., above 70° C., above 100° C., above 150° C., about 20° C., about 70° C., about 120° C., about 180° C., 20° C.-200° C., 20° C.-100° C., 100° C.-200° C., and/or 150° C.-200° C.

C33. The method of any of paragraphs C1-C6, wherein the adhering the test adherend includes curing the test adherend and the test adhesive at least partially concurrently.

C34. The method of any of paragraphs C1-C7, further comprising:
placing a crack starter between the test adhesive and the test adherend before the adhering the test adherend, optionally wherein the crack starter includes at least one of FEP, PTFE, and silicone.

C35. The method of paragraph C8, when depending from paragraph C1.4, wherein the crack starter is a first crack starter, wherein the placing a crack starter includes placing the first crack starter between the first test adhesive and the test adherend and includes placing a second crack starter between the second test adhesive and the test adherend, optionally wherein the second crack starter includes at least one of FEP, PTFE, and silicone.

C36. The method of any of paragraphs C8-C8.1, when depending from paragraph C1.5, wherein the crack starter is a first crack starter, wherein the placing a crack starter includes placing the first crack starter between the test adhesive and the first test adherend and includes placing a second crack starter between the test adhesive and the second test adherend, optionally wherein the second crack starter includes at least one of FEP, PTFE, and silicone.

C37. The method of any of paragraphs C8-C8.2, when depending from paragraph C2.12, wherein the crack starter is a first crack starter, wherein the placing a crack starter includes placing the first crack starter between the first test adhesive and the test adherend and includes placing a second crack starter between the second test adhesive and the test adherend, optionally wherein the second crack starter includes at least one of FEP, PTFE, and silicone.

C38. The method of any of paragraphs C8-C8.3, when depending from paragraph C2.13, wherein the crack starter is a first crack starter, wherein the placing a crack starter includes placing the first crack starter between the test adhesive and the first test adherend and includes placing a second crack starter between the test adhesive and the second test adherend, optionally wherein the second crack starter includes at least one of FEP, PTFE, and silicone.

C39. The method of any of paragraphs C8-C8.4, when depending from paragraph C2.14, wherein the crack starter is a first crack starter, wherein the placing a crack starter includes placing a second crack starter between the test adhesive and the peeling adherend, optionally wherein the second crack starter includes at least one of FEP, PTFE, and silicone.

C40. The method of any of paragraphs C1-C8.5, wherein the test adherend includes less than 20 plies, less than 10 plies, less than 8 plies, less than 6 plies, less than 4 plies, about 20 plies, about 10 plies, 8 plies, 6 plies, 4 plies, 3 plies, 2 plies, 1 ply, 1-20 plies, 1-8 plies, and/or 1-4 plies.

C41. The method of any of paragraphs C1-C9, wherein the first peeling support consists essentially of at least one of metal, aluminum alloy, and steel.

C42. The method of any of paragraphs C1-C10, wherein the second peeling support consists essentially of at least one of metal, aluminum alloy, and steel.

C43. The method of any of paragraphs C1-C11, further comprising:
fabricating the test adherend.

C44. The method of any of paragraphs C1-C12, further comprising:
curing the test adherend.

C45. The method of any of paragraphs C1-C13, wherein the test adherend is laminar and/or composite, and optionally wherein the test adherend includes at least one of a laminar material, a composite material, a fiber-reinforced plastic, a mineral-filled plastic, a polymeric material, a plastic, a glass, and a ceramic material.

C46. A layered test coupon fabricated according to any of the methods of paragraphs C1-C14.

C47. A layered test coupon comprising layers in the following sequence:
- a test structure including layers in the following sequence:
- a first peeling support,
- a test adhesive, and
- a test adherend that is non-metallic; and
- a second peeling support;
wherein the test adherend is coupled to the first peeling support with a test bond including the test adhesive, and wherein the second peeling support is bonded to the test adherend.

C47.1. The layered test coupon of paragraph C16, wherein the test adhesive is a first test adhesive, wherein the test bond is a first test bond, wherein the test structure includes the first test adhesive at a first location between the first peeling support and the test adherend, and includes a second test adhesive at a second location between the first peeling support and the test adherend, wherein the test adherend is coupled to the first peeling support with a second test bond including the second test adhesive.

C47.2. The layered test coupon of any of paragraphs C16-C16.1, wherein the test adherend is a first test adherend, wherein the test bond is a first test bond, wherein the test structure includes the first test adherend at a first location between the test adhesive and the second peeling support, and includes a second test adherend at a second location between the test adhesive and the second peeling support, wherein the second test adherend is coupled to the first peeling support with a second test bond including the test adhesive.

C48. A layered test coupon comprising layers in the following sequence:
- a first peeling support;
- a test structure including layers in the following sequence:
- a peeling adherend that is non-metallic,
- a test adhesive, and
- a test adherend that is non-metallic; and
- a second peeling support;
wherein the test adherend is coupled to the peeling adherend with a test bond including the test adhesive, wherein the first peeling support is bonded to the peeling adherend, and wherein the second peeling support is bonded to the test adherend.

C49. The layered test coupon of paragraph C17, further comprising:
- a structural adhesive between the peeling adherend and the first peeling support, optionally wherein the structural adhesive is at least one of a room temperature adhesive, a pressure sensitive adhesive, and a contact adhesive.

C50. The layered test coupon of any of paragraphs C17-C17.1, wherein the peeling adherend includes less than 20 plies, less than 10 plies, less than 8 plies, less than 6 plies, less than 4 plies, about 20 plies, about 10 plies, 8 plies, 6 plies, 4 plies, 3 plies, 2 plies, 1 ply, 1-20 plies, 1-8 plies, and/or 1-4 plies.

C50.1. The layered test coupon of any of paragraphs C17-C17.2, wherein the test adhesive is a first test adhesive, wherein the test bond is a first test bond, wherein the test structure includes the first test adhesive at a first location between the peeling adherend and the test adherend, and includes a second test adhesive at a second location between the peeling adherend and the test adherend, wherein the test adherend is coupled to the peeling adherend with a second test bond including the second test adhesive.

C50.2. The layered test coupon of any of paragraphs C17-C17.3, wherein the test adherend is a first test adherend, wherein the test bond is a first test bond, wherein the test structure includes the first test adherend at a first location between the test adhesive and the second peeling support, and includes a second test adherend at a second location between the test adhesive and the second peeling support, wherein the second test adherend is coupled to the peeling adherend with a second test bond including the test adhesive.

C50.3. The layered test coupon of any of paragraphs C17-C17.4, wherein the peeling adherend is substantially the same as the test adherend.

C50.4. The layered test coupon of any of paragraphs C17-C17.5, wherein the peeling adherend is laminar and/or composite, and optionally wherein the peeling adherend includes at least one of a laminar material, a composite material, a fiber-reinforced plastic, a mineral-filled plastic, a polymeric material, a plastic, a glass, and a ceramic material.

C51. The layered test coupon of any of paragraphs C16-C17.6, wherein the test structure has been subject to test conditions, wherein the test conditions include at least one of wetting, aging, and heating.

C52. The layered test coupon of any of paragraphs C16-C18, further comprising:
- a crack starter between the test adhesive and the test adherend, optionally wherein the crack starter includes at least one of FEP, PTFE, and silicone.

C53. The layered test coupon of paragraph C19, when depending from paragraph C15.1, wherein the crack starter is a first crack starter, further comprising:
- a second crack starter between the second test adhesive and the test adherend, optionally wherein the second crack starter includes at least one of FEP, PTFE, and silicone.

C54. The layered test coupon of any of paragraphs C19-C19.1, when depending from paragraph C15.2, wherein the crack starter is a first crack starter, further comprising:
- a second crack starter between the test adhesive and the second test adherend, optionally wherein the second crack starter includes at least one of FEP, PTFE, and silicone.

C55. The layered test coupon of any of paragraphs C19-C19.2, when depending from paragraph C16.3, wherein the crack starter is a first crack starter, further comprising:
- a second crack starter between the second test adhesive and the test adherend, optionally wherein the second crack starter includes at least one of FEP, PTFE, and silicone.

C56. The layered test coupon of any of paragraphs C19-C19.3, when depending from paragraph C16.4, wherein the crack starter is a first crack starter, further comprising:
- a second crack starter between the test adhesive and the second test adherend, optionally wherein the second crack starter includes at least one of FEP, PTFE, and silicone.

C57. The layered test coupon of any of paragraphs C19-C19.4, when depending from paragraph C16.5, wherein the crack starter is a first crack starter, further comprising:
- a second crack starter between the test adhesive and the peeling adherend, optionally wherein the second crack starter includes at least one of FEP, PTFE, and silicone.

C58. The layered test coupon of any of paragraphs C16-C19.5, wherein the test adherend includes less than 20 plies, less than 10 plies, less than 8 plies, less than 6 plies, less than 4 plies, about 20 plies, about 10 plies, 8 plies, 6 plies, 4 plies, 3 plies, 2 plies, 1 ply, 1-20 plies, 1-8 plies, and/or 1-4 plies.

C59. The layered test coupon of any of paragraphs C16-C20, wherein the first peeling support consists essentially of at least one of metal, aluminum alloy, and steel.

C60. The layered test coupon of any of paragraphs C16-C21, wherein the second peeling support consists essentially of at least one of metal, aluminum alloy, and steel.

C61. The layered test coupon of any of paragraphs C16-C22, further comprising:

a structural adhesive between the test adherend and the second peeling support, optionally wherein the structural adhesive is at least one of a room temperature adhesive, a pressure sensitive adhesive, and a contact adhesive.

C62. The layered test coupon of any of paragraphs C16-C23, wherein the test adherend is laminar and/or composite, and optionally wherein the test adherend includes at least one of a laminar material, a composite material, a fiber-reinforced plastic, a mineral-filled plastic, a polymeric material, a plastic, a glass, and a ceramic material.

C63. A method of testing a quality of a bond to non-metallic materials, the method comprising:

selecting the layered test coupon of any of paragraphs C15-C24; and peeling the first peeling support from the second peeling support to test a strength of the test bond.

C64. A method of testing a quality of a bond to non-metallic materials, the method comprising:

fabricating a layered test coupon according to the method of any of paragraphs C1-C14; and peeling the first peeling support from the second peeling support to test a strength of the test bond.

C65. The method of any of paragraphs C25-C26, when depending from C1.4, C1.5, C2.12, or C2.13, wherein the peeling includes partially peeling the first peeling support from the second peeling support to test a strength of the first test bond and includes partially peeling the first peeling support from the second peeling support to test a strength of the second test bond.

C66. The method of any of paragraphs C25-C27, further comprising:

initiating a crack in the test bond by applying a wedge between the first peeling support and the second peeling support.

C67. The method of any of paragraphs C25-C28, wherein the peeling includes attaching a peeling mechanism to the first peeling support and the second peeling support, and further includes applying a force with the peeling mechanism to peel the first peeling support from the second peeling support.

C68. The method of any of paragraphs C25-C29, wherein the peeling includes inserting a wedge between the first peeling support and the second peeling support, and further includes applying a force with the wedge to peel the first peeling support from the second peeling support.

C69. The method of any of paragraphs C25-C30, further comprising:

classifying a failure mode of the test bond, optionally wherein the classifying includes electronic imaging the test bond after the peeling.

C70. The method of any of paragraphs C25-C31, when depending from C1.4, C1.5, C2.12, or C2.13, further comprising:

classifying a failure mode of the second test bond, optionally wherein the classifying includes electronic imaging the second test bond after the peeling.

C71. The method of any of paragraphs C25-C32, further comprising:

quantifying an extent of failure of the test bond.

C71.1. The method of paragraph C33, wherein the quantifying includes electronic imaging the test bond after the peeling.

C71.2. The method of any of paragraphs C33-C33.1, wherein the quantifying includes determining at least one of a fraction of laminal failure, a fraction of interfacial failure, a fraction of cohesion failure, an extent of laminal failure, an extent of interfacial failure, and an extent of cohesion failure.

C72. The method of any of paragraphs C25-C33.2, when depending from C1.4, C1.5, C2.12, or C2.13, further comprising:

quantifying an extent of failure of the second test bond.

C72.1. The method of paragraph C34, wherein the quantifying includes electronic imaging the second test bond after the peeling.

C72.2. The method of any of paragraphs C34-C34.1, wherein the quantifying includes determining at least one of a fraction of laminal failure, a fraction of interfacial failure, a fraction of cohesion failure, an extent of laminal failure, an extent of interfacial failure, and an extent of cohesion failure.

C73. The method of any of paragraphs C25-C34.2, when depending from C1.4, C1.5, C2.12, or C2.13, further comprising:

comparing a failure mode of the first test bond and a failure mode of the second test bond.

C74. The method of any of paragraphs C25-C35, when depending from C1.4, C1.5, C2.12, or C2.13, further comprising:

comparing an extent of failure of the first test bond and an extent of failure of the second test bond.

D1. A method of fabricating a layered test coupon, the method comprising:

adhering a test adherend with a test adhesive to a shearing adherend to create a test bond and to form a test structure, wherein the test adherend is non-metallic, and wherein the shearing adherend is non-metallic;

bonding the shearing adherend to a first shearing support; and bonding the test adherend to a second shearing support.

D2. The method of paragraph D1, further comprising:

forming a first gap through the first shearing support and the shearing adherend;

forming a second gap, spaced apart from the first gap, through the second shearing support and the test adherend;

wherein the first gap and the second gap define a shearing test region where the first shearing support, the shearing adherend, the test adhesive, the test adherend, and the second shearing support are intact.

D3. The method of any of paragraphs D1-D2, further comprising:

applying test conditions to the test structure prior to the bonding the shearing adherend and the bonding the test adherend, optionally wherein the applying includes at least one of wetting, aging, and heating.

D3.1. The method of paragraph D3, wherein the applying is performed for less than 100 days, less than 50 days, less than 20 days, less than 15 days, less than 10 days, less than 200 hours, less than 150 hours, less than 100 hours, at least 48 hours, at least 72 hours, at least 100 hours, at least 150 hours, at least 200 hours, at least 10 days, 48 hours—100 days, 48 hours—20 days, and/or 100 hours—20 days.

D4. The method of any of paragraphs D1-D3, wherein the bonding the shearing adherend includes curing the shearing adherend onto the first shearing support.

D5. The method of any of paragraphs D1-D4, wherein the bonding the test adherend includes curing the test adherend onto the second shearing support.

D6. The method of any of paragraphs D1-D5, wherein the bonding the shearing adherend and the adhering the test adherend are performed at least partially concurrently.

D7. The method of any of paragraphs D1-D6, wherein the bonding the test adherend and the adhering the test adherend are performed at least partially concurrently.

D8. The method of any of paragraphs D1-D7, wherein the bonding the shearing adherend and the bonding the test adherend are performed at least partially concurrently.

D9. The method of any of paragraphs D1-D8, wherein the bonding the shearing adherend includes applying a structural adhesive between the shearing adherend and the first shearing support, and optionally includes curing the structural adhesive.

D9.1. The method of paragraph D9, wherein the structural adhesive is at least one of a room temperature adhesive, a pressure sensitive adhesive, and a contact adhesive.

D10. The method of any of paragraphs D1-D9.1, wherein the bonding the test adherend includes applying a structural adhesive between the test adherend and the second shearing support, and optionally includes curing the structural adhesive.

D10.1. The method of paragraph D10, wherein the structural adhesive is at least one of a room temperature adhesive, a pressure sensitive adhesive, and a contact adhesive.

D11. The method of any of paragraphs D1-D10.1, wherein the adhering the test adherend includes applying the test adhesive between the test adherend and the shearing adherend.

D12. The method of any of paragraphs D1-D11, wherein the shearing adherend includes less than 20 plies, less than 10 plies, less than 8 plies, less than 6 plies, less than 4 plies, about 20 plies, about 10 plies, 8 plies, 6 plies, 4 plies, 3 plies, 2 plies, 1 ply, 1-20 plies, 1-8 plies, and/or 1-4 plies.

D13. The method of any of paragraphs D1-D12, wherein the test adherend includes less than 20 plies, less than 10 plies, less than 8 plies, less than 6 plies, less than 4 plies, about 20 plies, about 10 plies, 8 plies, 6 plies, 4 plies, 3 plies, 2 plies, 1 ply, 1-20 plies, 1-8 plies, and/or 1-4 plies.

D14. The method of any of paragraphs D1-D13, wherein the adhering the test adherend includes curing the test adhesive, optionally at a temperature above 20° C., above 70° C., above 100° C., above 150° C., about 20° C., about 70° C., about 120° C., about 180° C., 20° C.-200° C., 20° C.-100° C., 100° C.-200° C., and/or 150° C.-200° C.

D15. The method of any of paragraphs D1-D14, wherein the adhering the test adherend includes curing the shearing adherend and the test adhesive at least partially concurrently.

D16. The method of any of paragraphs D1-D15, wherein the adhering the test adherend includes curing the test adherend and the test adhesive at least partially concurrently.

D17. The method of any of paragraphs D1-D16, wherein the shearing adherend is substantially the same as the test adherend.

D18. The method of any of paragraphs D1-D17, wherein the first shearing support consists essentially of at least one of metal, aluminum alloy, and steel.

D19. The method of any of paragraphs D1-D18, wherein the second shearing support consists essentially of at least one of metal, aluminum alloy, and steel.

D20. The method of any of paragraphs D1-D19, further comprising:
fabricating the shearing adherend.

D21. The method of any of paragraphs D1-D20, further comprising:
fabricating the test adherend.

D22. The method of any of paragraphs D1-D21, further comprising:
curing the shearing adherend.

D23. The method of any of paragraphs D1-D22, further comprising:
curing the test adherend.

D24. The method of any of paragraphs D1-D23, further comprising:
preparing a surface of the test adherend for adhering to the shearing adherend.

D24.1. The method of paragraph D24, wherein the preparing includes peeling a peel ply from the test adherend.

D25. The method of any of paragraphs D1-D24.1, wherein the test adherend is laminar and/or composite, and optionally wherein the test adherend includes at least one of a laminar material, a composite material, a fiber-reinforced plastic, a mineral-filled plastic, a polymeric material, a plastic, a glass, and a ceramic material.

D26. The method of any of paragraphs D1-D25, wherein the shearing adherend is laminar and/or composite, and optionally wherein the shearing adherend includes at least one of a laminar material, a composite material, a fiber-reinforced plastic, a mineral-filled plastic, a polymeric material, a plastic, a glass, and a ceramic material.

D27. A layered test coupon fabricated according to any of the methods of paragraphs D1-D26.

D28. A layered test coupon comprising layers in the following sequence:
a first shearing support;
a test structure including layers in the following sequence:
a shearing adherend that is non-metallic,
a test adhesive, and
a test adherend that is non-metallic; and
a second shearing support;
wherein the test adherend is coupled to the shearing adherend with a test bond including the test adhesive, wherein the first shearing support is bonded to the shearing adherend, and wherein the second shearing support is bonded to the test adherend.

D28.1. The layered test coupon of paragraph D28, wherein the layered test coupon defines a shearing test region between a first gap traversing the first shearing support and the shearing adherend, and a second gap, spaced apart from the first gap, traversing the test adherend and the second shearing support.

D28.2. The layered test coupon of any of paragraphs D28-D28.1, wherein the test structure has been subject to test conditions, wherein the test conditions include at least one of wetting, aging, and heating.

D28.3. The layered test coupon of any of paragraphs D28-D28.2, further comprising:
a first structural adhesive between the shearing adherend and the first shearing support, optionally wherein the first structural adhesive is at least one of a room temperature adhesive, a pressure sensitive adhesive, and a contact adhesive.

D28.4. The layered test coupon of any of paragraphs D28-D28.3, further comprising:
a second structural adhesive between the test adherend and the second shearing support, optionally wherein the second structural adhesive is at least one of a room temperature adhesive, a pressure sensitive adhesive, and a contact adhesive.

D28.5. The layered test coupon of any of paragraphs D28-D28.4, wherein the shearing adherend includes less than 20 plies, less than 10 plies, less than 8 plies, less than 6 plies, less than 4 plies, about 20 plies, about 10 plies, 8 plies, 6 plies, 4 plies, 3 plies, 2 plies, 1 ply, 1-20 plies, 1-8 plies, and/or 1-4 plies.

D28.6. The layered test coupon of any of paragraphs D28-D28.5, wherein the test adherend includes less than 20 plies, less than 10 plies, less than 8 plies, less than 6 plies, less than 4 plies, about 20 plies, about 10 plies, 8 plies, 6 plies, 4 plies, 3 plies, 2 plies, 1 ply, 1-20 plies, 1-8 plies, and/or 1-4 plies.

D28.7. The layered test coupon of any of paragraphs D28-D28.6, wherein the shearing adherend is substantially the same as the test adherend.

D28.8. The layered test coupon of any of paragraphs D28-D28.7, wherein the first shearing support consists essentially of at least one of metal, aluminum alloy, and steel.

D28.9. The layered test coupon of any of paragraphs D28-D28.8, wherein the second shearing support consists essentially of at least one of metal, aluminum alloy, and steel.

D28.10. The layered test coupon of any of paragraphs D28-D28.9, wherein the test adherend is laminar and/or composite, and optionally wherein the test adherend includes at least one of a laminar material, a composite material, a fiber-reinforced plastic, a mineral-filled plastic, a polymeric material, a plastic, a glass, and a ceramic material.

D28.11. The layered test coupon of any of paragraphs D28-D28.10, wherein the shearing adherend is laminar and/or composite, and optionally wherein the shearing adherend includes at least one of a laminar material, a composite material, a fiber-reinforced plastic, a mineral-filled plastic, a polymeric material, a plastic, a glass, and a ceramic material.

D29. A method of testing a quality of a bond to non-metallic materials, the method comprising:
selecting the layered test coupon of any of paragraphs D27-D28.11; and
shearing the test bond to test a strength of the test bond.

D30. A method of testing a quality of a bond to non-metallic materials, the method comprising:
fabricating a layered test coupon according to the method of any of paragraphs D1-D26; and
shearing the test bond to test a strength of the test bond.

D31. The method of any of paragraphs D29-D30, wherein the shearing includes attaching a shearing mechanism to the first shearing support and the second shearing support, and further includes applying a force with the shearing mechanism to shear the test bond.

D32. The method of any of paragraphs D29-D31, further comprising:
classifying a failure mode of the test bond, optionally wherein the classifying includes electronic imaging the test bond after the shearing.

D33. The method of any of paragraphs D29-D32, further comprising:
quantifying an extent of failure of the test bond.

D33.1. The method of paragraph D33, wherein the quantifying includes electronic imaging the test bond after the shearing.

D33.2. The method of any of paragraphs D33-D33.1, wherein the quantifying includes determining at least one of a fraction of laminal failure, a fraction of interfacial failure, a fraction of cohesion failure, an extent of laminal failure, an extent of interfacial failure, and an extent of cohesion failure.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa. Similarly, subject matter that is recited as being configured to perform a particular function may additionally or alternatively be described as being operative to perform that function.

The various disclosed elements of apparatuses and steps of methods disclosed herein are not required to all apparatuses and methods according to the present disclosure, and the present disclosure includes all novel and non-obvious combinations and subcombinations of the various elements and steps disclosed herein. Moreover, one or more of the various elements and steps disclosed herein may define independent inventive subject matter that is separate and apart from the whole of a disclosed apparatus or method. Accordingly, such inventive subject matter is not required to be associated with the specific apparatuses and methods that are expressly disclosed herein, and such inventive subject matter may find utility in apparatuses and/or methods that are not expressly disclosed herein.

The invention claimed is:

1. A method of testing a quality of a bond to non-metallic materials, the method comprising:
fabricating a layered test coupon by:
adhering a test adherend with a first test adhesive to a first location on a peeling adherend to create a first test bond and adhering the test adherend with a second test adhesive to a second location on the peeling adherend to create a second test bond, wherein the test adherend is laminar, wherein the peeling adherend is laminar, and wherein together the test adherend, the first test adhesive, the first test bond, the second test adhesive, the second test bond, and the peeling adherend form a test structure;
bonding the peeling adherend to a first peeling support; and
bonding the test adherend to a second peeling support;
partially peeling the first peeling support from the second peeling support to test a strength of the first test bond; and
partially peeling the first peeling support from the second peeling support to test a strength of the second test bond.

2. The method of claim 1, further comprising:
applying test conditions to the test structure prior to the bonding the peeling adherend and the bonding the test adherend, wherein the applying includes at least one of wetting, aging, and heating.

3. The method of claim 2, wherein the applying is performed for less than 20 days.

4. The method of claim 1, wherein the bonding the peeling adherend includes applying a room temperature adhesive between the peeling adherend and the first peeling support, and wherein the bonding the test adherend includes applying a room temperature adhesive between the test adherend and the second peeling support.

5. The method of claim 1, further comprising:
quantifying an extent of failure of the first test bond by electronic imaging the first test bond after partially peeling to test the strength of the first test bond; and
quantifying an extent of failure of the second test bond by electronic imaging the second test bond after partially peeling to test the strength of the second test bond.

6. The method of claim 1, wherein the test adherend includes less than 6 plies and wherein the peeling adherend includes less than 6 plies.

7. The method of claim 6, wherein the test adherend and the peeling adherend have an equal number of plies.

8. The method of claim 1, wherein the peeling adherend is substantially the same as the test adherend.

9. A method of testing a quality of a bond to non-metallic materials, the method comprising:
fabricating a layered test coupon by:
adhering a first test adherend with a test adhesive to a first location on a peeling adherend to create a first test bond and adhering a second test adherend with the test adhesive to a second location on the peeling adherend to create a second test bond, wherein the first test adherend is laminar, wherein the second test adherend is laminar, wherein the peeling adherend is laminar, and wherein together the test adhesive, the first test adherend, the first test bond, the second test adherend, the second test bond, and the peeling adherend form a test structure;
bonding the peeling adherend to a first peeling support; and
bonding the first test adherend and the second test adherend to a second peeling support;
partially peeling the first peeling support from the second peeling support to test a strength of the first test bond; and
partially peeling the first peeling support from the second peeling support to test a strength of the second test bond.

10. The method of claim 9, further comprising:
applying test conditions to the test structure prior to the bonding to the first peeling support and the bonding to the second peeling support, wherein the applying includes at least one of wetting, aging, and heating.

11. The method of claim 10, wherein the applying is performed for less than 20 days.

12. The method of claim 9, wherein the bonding the peeling adherend includes applying a room temperature adhesive between the peeling adherend and the first peeling support, and wherein the bonding the first test adherend and the second test adherend includes applying a room temperature adhesive between the first test adherend and the second peeling support and applying the room temperature adhesive between the second test adherend and the second peeling support.

13. The method of claim 9, further comprising:
quantifying an extent of failure of the first test bond by electronic imaging the first test bond after partially peeling to test the strength of the first test bond; and
quantifying an extent of failure of the second test bond by electronic imaging the second test bond after partially peeling to test the strength of the second test bond.

14. The method of claim 9, wherein the first test adherend includes less than 6 plies, wherein the second test adherend includes less than 6 plies, and wherein the peeling adherend includes less than 6 plies.

15. The method of claim 9, wherein the first test adherend and the second test adherend have an equal number of plies.

16. The method of claim 15, wherein the first test adherend, the second test adherend, and the peeling adherend have an equal number of plies.

* * * * *